(12) United States Patent
Sheth et al.

(10) Patent No.: US 10,793,820 B2
(45) Date of Patent: Oct. 6, 2020

(54) MINIATURIZED, AUTOMATED IN-VITRO TISSUE BIOREACTOR

(71) Applicant: Lawrence Livermore National Security, LLC, Livermore, CA (US)

(72) Inventors: Heeral Sheth, San Francisco, CA (US); Haiyin Chen, San Ramon, CA (US); Bryan D. Hudson, Livermore, CA (US); Kris Kulp, Livermore, CA (US); Margaret W. Mcnerney, Pleasanton, CA (US); Satinderpall S. Pannu, Pleasanton, CA (US); Fang Qian, Santa Cruz, CA (US); Angela C. Tooker, Dublin, CA (US); Elizabeth K. Wheeler, Livermore, CA (US); Vanessa Tolosa, Emeryville, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 970 days.

(21) Appl. No.: 14/265,019

(22) Filed: Apr. 29, 2014

(65) Prior Publication Data

US 2014/0322701 A1 Oct. 30, 2014

Related U.S. Application Data

(60) Provisional application No. 61/817,812, filed on Apr. 30, 2013.

(51) Int. Cl.
*C12M 3/00* (2006.01)
*C12M 3/06* (2006.01)
(Continued)

(52) U.S. Cl.
CPC ............ *C12M 35/02* (2013.01); *C12M 41/26* (2013.01); *C12M 41/46* (2013.01); *C12M 41/48* (2013.01)

(58) Field of Classification Search
None
See application file for complete search history.

(56) References Cited

U.S. PATENT DOCUMENTS 4,695,547 A * 9/1987 Hilliard .................. C12M 23/12
204/242
6,176,874 B1 1/2001 Vacanti et al.
(Continued)

FOREIGN PATENT DOCUMENTS

WO WO-2012043820 A1 * 4/2012 ......... G01N 33/5088

OTHER PUBLICATIONS

Witting Jr. et al. (A reusable microfluidic plate with alternate-choice architecture for assessing growth preference in tissue culture, 14 (2005) 79-89).*

(Continued)

*Primary Examiner* — Liban M Hassan
(74) *Attorney, Agent, or Firm* — Zilka-Kotab, P.C.

(57) ABSTRACT

In one embodiment, a system includes a bioreactor coupled to a substrate. The bioreactor includes: a plurality of walls defining a reservoir; a plurality of fluidic channels in at least some of the walls; a fluidic inlet in fluidic communication with the reservoir via, the fluidic channels; a fluidic outlet in fluidic communication with the reservoir via the fluidic channels; and one or more sensors coupled to the reservoir, each sensor being configured to detect one or more of: environmental conditions in the reservoir; and physiological conditions of one or more cells optionally present in the reservoir. In another embodiment, a method includes delivering media to a reservoir of a bioreactor; delivering a plurality of cells to the reservoir, controlling a reservoir temperature and a reservoir gas composition; using one or more (Continued)

(front view)

more of the sensors to monitor environmental and physiological conditions; and reporting the environmental and/or physiological conditions.

22 Claims, 12 Drawing Sheets

(51) Int. Cl.
*C12M 1/42* (2006.01)
*C12M 1/34* (2006.01)
*C12M 1/36* (2006.01)

(56) References Cited

U.S. PATENT DOCUMENTS

| | | | | |
|---|---|---|---|---|
| 2001/0048900 | A1* | 12/2001 | Bardell | B01D 11/00 422/400 |
| 2002/0025547 | A1* | 2/2002 | Rao | C12M 23/12 435/40.5 |
| 2002/0028478 | A1* | 3/2002 | Lehmann | C12M 23/16 435/29 |
| 2004/0029258 | A1* | 2/2004 | Heaney | B01L 3/5025 435/287.2 |
| 2004/0077075 | A1* | 4/2004 | Jensen | B01L 3/5027 435/297.2 |
| 2005/0019898 | A1* | 1/2005 | Adey | B01F 5/10 435/286.7 |
| 2005/0089924 | A1* | 4/2005 | Ho | B01L 3/5027 435/7.1 |
| 2005/0118705 | A1* | 6/2005 | Rabbitt | B01L 3/502761 435/287.1 |
| 2006/0188904 | A1* | 8/2006 | Ozkan | C12Q 1/6825 435/6.11 |
| 2006/0257993 | A1* | 11/2006 | McDevitt | B01L 3/502715 435/287.2 |
| 2007/0099294 | A1* | 5/2007 | Yang | C12M 23/12 435/299.1 |
| 2007/0254004 | A1* | 11/2007 | Rosero | A61B 5/076 424/423 |
| 2008/0032380 | A1* | 2/2008 | Kleis | C12M 23/04 435/243 |
| 2008/0160601 | A1* | 7/2008 | Handique | B01L 3/502715 435/287.2 |
| 2008/0248514 | A1* | 10/2008 | Inamori | C12N 9/0006 435/26 |
| 2008/0299539 | A1* | 12/2008 | Lee | B01F 11/0045 435/3 |
| 2009/0265287 | A1* | 10/2009 | Haas | G06K 9/00536 706/3 |
| 2010/0006451 | A1* | 1/2010 | Gordon | G01N 33/5438 205/777.5 |
| 2010/0068822 | A1* | 3/2010 | Heydenhauss | B01L 3/50273 436/172 |
| 2010/0103410 | A1* | 4/2010 | Silbergleit | B01L 3/5085 356/246 |
| 2010/0120626 | A1* | 5/2010 | Ross | C12N 13/00 506/7 |
| 2010/0317548 | A1* | 12/2010 | Huang | C12M 35/02 506/40 |
| 2011/0033918 | A1* | 2/2011 | Asnaghi | C12M 21/08 435/289.1 |
| 2011/0044865 | A1* | 2/2011 | Groisman | B01L 9/527 422/503 |
| 2011/0112232 | A1* | 5/2011 | Krishna | B01J 35/004 524/424 |
| 2011/0217771 | A1* | 9/2011 | Thorslund | C12M 23/10 435/325 |
| 2013/0230881 | A1* | 9/2013 | Yasuda | G01N 33/5088 435/29 |
| 2015/0050686 | A1 | 2/2015 | Sheth et al. | |

OTHER PUBLICATIONS

Rodrigues et al. (Cell-based microfluidic biochip for the electrochemical real-time monitoring of glucose and oxygen, 132 (2008) 608-613).*
Rolston et al. (A low-cost multielectrode system for data acquisition enabling real-time closed-loop processing with rapid recovery from stimulation artifacts, (2009) 1-17) (Year: 2009).*
Nalayanda et al., "Engineering an artificial alveolar-capillary membrane:a novel continuously perfused model within microchannels," Journal of Pediatric Surgery, 45, pp. 45-51 (Year: 2010).*
Black et al., "In vitro reconstruction of a human capillary like network in a tissue-engineered skin equivalent," The FASEB Journal, vol. 12, 1998, pp. 1331-1340.
Borenstein et al., "Microfabrication Technology for Vascularized Tissue Engineering," Biomedical Microdevices, vol. 4, No. 3, 2002, pp. 167-175.
Campbell et al., "Tissue engineering with the aid of inkjet printers," Expert Opinion on Biological Therapy, vol. 7, No. 3, 2007, pp. 1123-1127.
Ehrbar et al., "Cell-Demanded Liberation of Vegf121 From Fibrin Implants Induces Local and Controlled Blood Vessel Growth," Journal of American Heart Association, 2004, pp. 1-18.
Griffith et al., "Tissue Engineering—Current Challenges and Expanding Opportunities," Science, vol. 295, 2002, pp. 1009-1016.
Hudson, J.B., "Surface Science: an introduction," 1992, pp. 1-321.
Ko et al., "Engineering Thick Tissues—The Vascularisation Problem," European Cells and Materials, vol. 14, 2007, pp. 1-19.
Kola et al., "Can the pharmaceutical industry reduce attrition rates?," Nature Reviews Drug Discovery, vol. 3, 2004, pp. 711-715.
Lokmic et al., "Engineering the Microcirculation," Tissue Engineering: Part B, vol. 14, No. 1, 2008, pp. 87-103.
Mironov et al., "Organ printing: promises and challenges," Regen. Med, vol. 3, No. 1, 2008, pp. 93-103.
Muschler et al., "Engineering Principles of Clinical Cell-Based Tissue Engineering," The Journal of Bone and Joint Surgery, vol. 86-A, No. 7, 2004, pp. 1541-1558.
Norotte et al., "Scaffold-free vascular tissue engineering using bioprinting," Biomaterials, vol. 30, 2009, pp. 5910-5917.
Novosel et al., "Vascularization is the key challenge in tissue engineering," Advanced Drug Delivery Reviews, vol. 63, 2011, pp. 300-311.
Ogawa et al., "Vascular tissue engineering and vascularized 3D tissue regeneration," Regen. Med., vol. 2, No. 5, pp. 831-837.
Peters et al., "Engineering vascular networks in porous polymer matrices," Journal of Biomedical Materials Research, vol. 60, 2002, pp. 668-678.
Yang et al., "Growth in primary culture of mouse submandibular epithelial cells embedded in collagen gels," In Vitro, vol. 18, No. 5, 1982, pp. 435-442.
Yannas, I.V., "Tissue Organ Regeneration in Adults," Springer, 2001, pp. 1-379.
Sheth et al., U.S. Appl. No. 14/452,453, filed Aug. 5, 2014.
Atala et al., "Tissue-engineered autologous bladders for patients needing cystoplasty," www.thelancet.com, vol. 367, Apr. 15, 2006, pp. 1241-1246.
Boland et al., "Application of inkjet printing to tissue engineering," Biotechnology Journal, 2006, vol. 1, pp. 910-917.
Chambard et al., "Influence of Collagen Gel on the Orientation of Epithelial Cell Polarity: Follicle Formation from Isolated Thyroid Cells and from Preformed Monolayers," The Journal of Cell Biology, vol. 91, Oct. 1981, pp. 157-166.
Chrobak et al., "Formation of perfused, functional microvascular tubes in vitro," Microvascular Research, vol. 71, 2006, pp. 185-196.
Gauvin et al., "Application of microtechnologies for the vascularization of engineered tissues," Vascular Cell, vol. 3, No. 24, 2011, pp. 1-7.
Haeuptle et al., "Effect of Cell Shape Change on the Function and Differentiation of Rabbit Mammary Cells in Culture," The Journal of Cell Biology, vol. 96, May 1983, pp. 1425-1434.

(56) References Cited

OTHER PUBLICATIONS

Hall et al., "Lumen formation by epithelial cell lines in response to collagen overlay: A morphogenetic model in culture," Proceedings of the National Academy of Sciences, vol. 79, Aug. 1982, pp. 4672-4676.
Haraguchi et al., "Development of a New Assay System for Evaluating the Permeability of Various Substances Through Three-Dimensional Tissue," Tissue Engineering: Part C, vol. 16, No. 4, 2010, pp. 685-693.
Iguchi et al., "Growth of normal mouse vaginal epithelial cells in and on collagen gels," Proceedings of the National Academy of Sciences, vol. 80, Jun. 1983, pp. 3743-3747.
Jakab et al., "Organ printing: Fiction or science," Biorheology, vol. 41, 2004, pp. 371-375.
Jakab et al., "Tissue engineering by self-assembly and bio-printing of living cells," Biofabrication, vol. 2, 2010, pp. 1-14.
Kenter et al., "Establishing risk of human experimentation with drugs: lessons from TGN1412," www.thelancet.com, vol. 368, Oct. 14, 2006, pp. 1387-1391.
Langer et al., "Tissue Engineering," Science, vol. 260, May 14, 1993, pp. 920-926.
Mironov et al., "Bioprinting: A Beginning," Tissue Engineering, vol. 12, No. 4, 2006, pp. 631-637.
Mironov et al., "Organ printing: computer-aided jet-based 3D tissue engineering," TRENDS in Biotechnology, vol. 21, No. 4, Apr. 2003, pp. 157-161.
Mironov et al., "Organ printing: Tissue spheroids as building bocks," Biomaterials, vol. 30, 2009, pp. 2164-2174.
Montesano et al., "Collagen Matrix Promotes Reorganization of Pancreatic Endocrine Cell Monolayers into Islet-like Organoids," The Journal of Cell Biology, vol. 97, Sep. 1983, pp. 935-939.
Montesano et al., "In Vitro Rapid Organization of Endothelial Cells into Capillary-like Networks Is Promoted by Collagen Matrices," The Journal of Cell Biology, vol. 97, Nov. 1983, pp. 1648-1652.
Mooney et al., "Growing New Organs," Scientific American, Apr. 1999, pp. 60-65.
Nakamura et al., "Biocompatible Inkjet Printing Technique for Designed Seeding of Individual Living Cells," Tissue Engineering, vol. 11, No. 11/12, 2005, pp. 1658-1671.
Nishiyama et al., "Development of a Three-Dimensional Bioprinter: Construction of Cell Supporting Structures Using Hydrogel and State-of-the-Art Inkjet Technology," Journal of Biomechanical Engineering, vol. 131, Mar. 2009, pp. 035001-1/035001-6.
Phillippi et al., "Microenvironments Engineered by Inkjet Bioprinting Spatially Direct Adult Stem Cells Toward Muscle-and Bone-Like Subpopulations," Stem Cells, vol. 26, 2008, pp. 127-134.
Rivron et al., "Engineering Vascularised Tissues In Vitro," European Cells and Materials, vol. 15, 2008, pp. 27-40.
Rouwkema et al., "Vascularization in tissue engineering," Cell Press, Jun. 26, 2008, pp. 434-441.
Saunders et al., "Delivery of human fibroblast cells by piezoelectric drop-on-demand inkjet printing," Biomaterials, vol. 29, 2008, pp. 193-203.
Smith et al., "Characterizing Environmental Factors that Impact the Viability of Tissue-Engineered Constructs Fabricated by a Direct-Write Bioassembly Tool," Tissue Engineering, vol. 13, No. 2, 2007, pp. 373-186.
Smith et al., "Three-Dimensional BioAssembly Tool for Generating Viable Tissue-Engineered Constructs," Tissue Engineering, vol. 10, No. 9110, 2004, pp. 1566-1578.
Wu et al., "Omnidirectional Printing of 3D Microvascular Networks," Advanced Materials, 2011, pp. 1-6.
Xu et al., "Inkjet printing of viable mammalian cells," Biomaterials, vol. 26, 2005, pp. 93-99.
Xu et al., "Viability and electrophysiology of neural cell structures generated by the inkjet printing method," Biomaterials, vol. 27, 2006, pp. 3580-3588.
Yamazoe et al., "Cell micropatterning on an albumin-based substrate using an inkjet printing technique," Journal of Biomedical Materials Research Part A, Jan. 15, 2009, pp. 1202-1209.
Yang et al., "Sustained growth and three-dimensional organization of primary mammary tumor epithelial cells embedded in collagen gels," Proceedings of the National Academy of Sciences, vol. 76, No. 7, Jul. 1979, pp. 3401-3405.
Restriction Requirement from U.S. Appl. No. 14/452,453, dated Mar. 15, 2016.
Yang et al., "Growth of cultured cells using collagen as substrate," International Review of Cytology, vol. 81, 1983, pp. 249-286.
Non-Final Office Action from U.S. Appl. No. 14/452,453, dated Jul. 28, 2016.
Resende, P., "Draper develops 'brain-on-a-chip' to study brain diseases," Boston Business Journal, Oct. 23, 2012, retrieved from http://www.bizjournals.com/boston/blog/mass-high-tech/2012/10/draper-develops-brain-on-a-chip-to-study.html?page=all, pp. 1-4.
Yang et al., "Sustained growth in primary culture of normal mammary epithelial cells embedded in collagen gels," Proceedings of the National Academy of Sciences, vol. 77, No. 4, Apr. 1980, pp. 2088-2092.
Yang et al., "Three-dimensional growth and morphogenesis of mouse submandibular epithelial cells in serum-free primary culture," Experimental Cell Research, vol. 137, 1982, pp. 481-485.
Final Office Action from U.S. Appl. No. 14/452,453, dated Feb. 22, 2017.
Ferris et al., "Biofabrication: an overview of the approaches used for printing of living cells," Applied Microbiology and Biotechnology, vol. 97, Mar. 2013, pp. 4243-4258.
Non-Final Office Action from U.S. Appl. No. 14/452,453, dated Jun. 22, 2018.
Tibbitt et al., "Hydrogels as Extracellular Matrix Mimics for 3D Cell Culture," Biotechnology and Bioengineering, vol. 103, No. 4, Jul. 1, 2009, pp. 655-663.
Alberts et al., "Blood Vessels and Endothelial Cells," Molecular Biology of the Cell, NCBI Bookshelf, 2002, 5 pages.
Final Office Action from U.S. Appl. No. 14/452,453, dated Mar. 15, 2019.
Frantz et al., "The extracellular matrix at a glance," Journal of Cell Science, Cell Science at a Glance, 2010, pp. 4195-4200.
Examiner's Answer to Appeal Brief from U.S. Appl. No. 14/452,453, dated Dec. 10, 2019.

\* cited by examiner (front view)

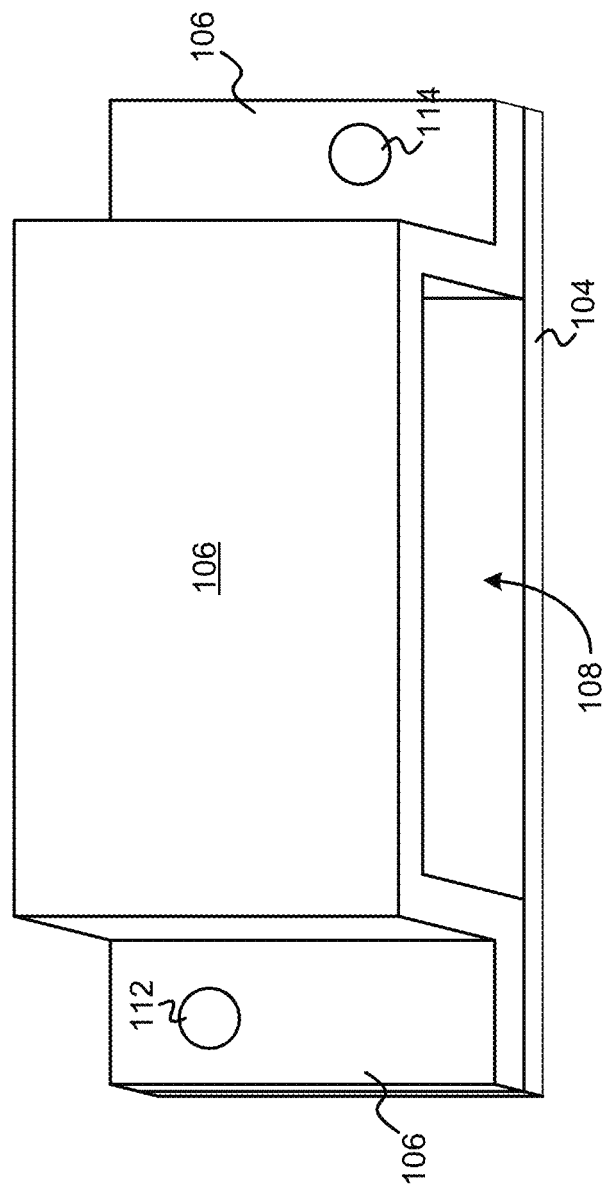
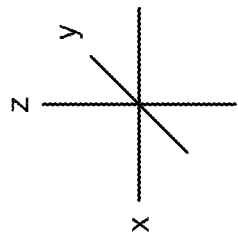
FIG. 1A (top view)

(side view)

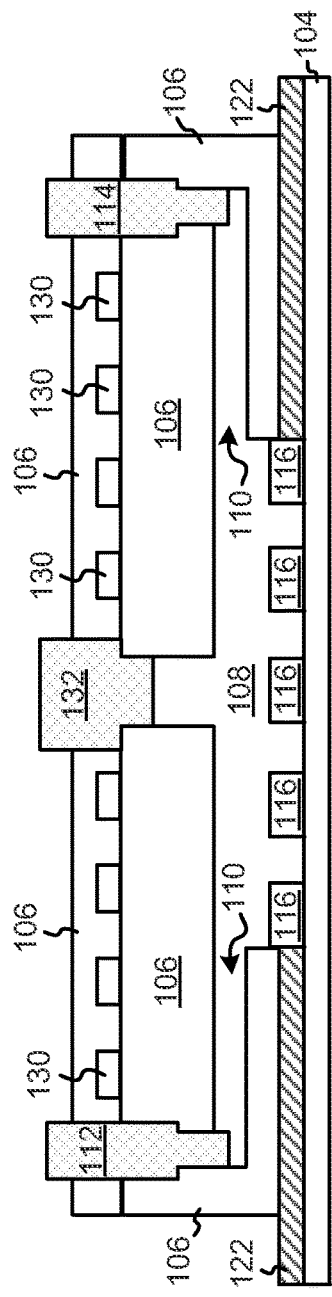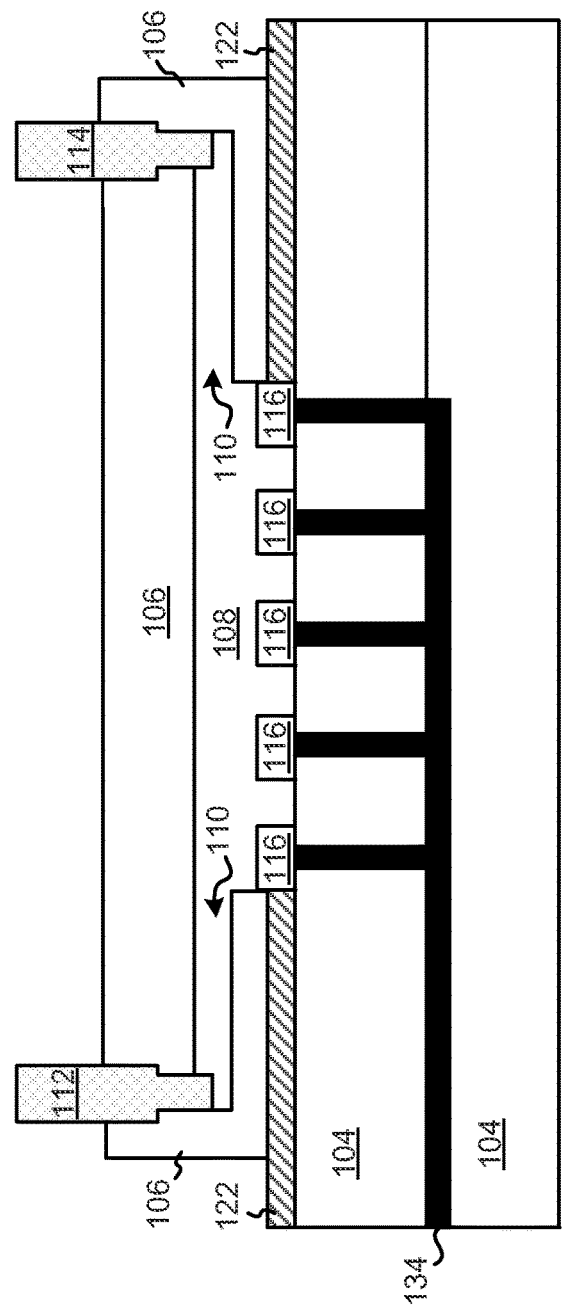

MINIATURIZED, AUTOMATED IN-VITRO TISSUE BIOREACTOR

RELATED APPLICATIONS

The present application claims priority to U.S. Provisional Application No. 61/817,812 filed Apr. 30, 2013, which is incorporated herein by reference in its entirety.

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to cell biology, and more particularly, this invention relates to systems and methods for controlling and monitoring conditions in a cell and tissue culture environment using an in-vitro tissue bioreactor with integrated electrical stimulation, chemical sensing, and environmental and fluidic controls.

BACKGROUND

The microbiology field is, as with many technical fields, continuously advancing and incorporating advances in other fields to useful applications such as cell and tissue culture. More recent advances include the ability to culture human cells and tissue on organ scaffolds to create functioning organs de novo.

These advances have significant applications for the pharmaceutical and medical field, since the ability to culture human cells and tissues with increasing precision opens new avenues for more efficient and effective clinical therapies. Currently, development of new therapeutics takes over a decade and costs are commonly on the billion-dollar scale. Less than 1% of potential new pharmaceuticals reach market and greater than 10% of those that reach market demonstrate serious unanticipated adverse effects that cause market withdrawal and significant costs in litigation.

Accordingly, it would be of great benefit to provide a platform with in situ sensing and diagnostics for rapid, efficient, and easily replicable in-vitro cell culture to improve the ability to evaluate the impact of exposing cells to various stresses, chemicals, and the like while monitoring in real time the impact on the cells.

SUMMARY

In one embodiment, a system includes a bioreactor coupled to a substrate. The bioreactor includes: a plurality of walls defining a reservoir; a plurality of fluidic channels in at least some of the walls; a fluidic inlet in fluidic communication with the reservoir via the fluidic channels; a fluidic outlet in fluidic communication with the reservoir via the fluidic channels; and one or more sensors coupled to the reservoir, each sensor being configured to detect one or more of: environmental conditions in the reservoir; and physiological conditions of one or more cells optionally present in the reservoir.

In another embodiment, a method includes delivering media to a reservoir of a bioreactor; delivering a plurality of cells to the reservoir, wherein at least some of the cells are disposed onto one or more sensors in the bioreactor; controlling a reservoir temperature and a reservoir gas composition; using one or more of the sensors to monitor one or more of: environmental conditions in the reservoir, and physiological conditions of at least some of the cells; and communicating the monitored environmental conditions and/or physiological conditions to an external device.

BRIEF DESCRIPTION OF THE DRAWINGS

FIG. 2D depicts a side view of a simplified schematic of a bioreactor having an open-top configuration and a plurality of gas-exchange channels, according to one embodiment.

FIG. 2E depicts a side view of a simplified schematic of a bioreactor having a closed-top configuration and a plurality of vacuum channels, according to one embodiment.

DETAILED DESCRIPTION

Figure 1:
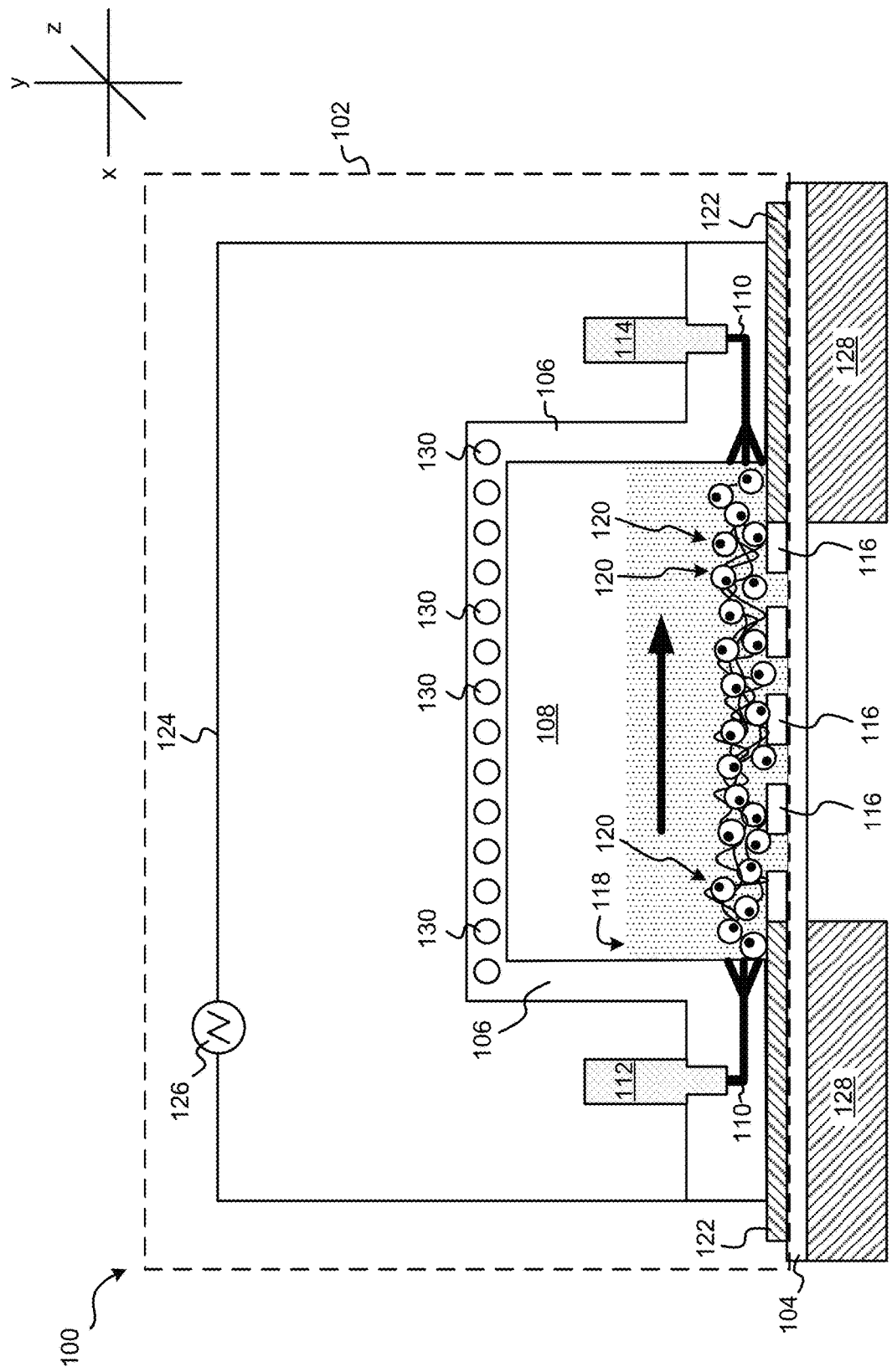
FIGS. 1-1B are simplified schematics of a bioreactor shown from a front view (FIG. 1), a top view (FIG. 1A) and a side view (FIG. 1B), according to several embodiments.
Figure 1B:
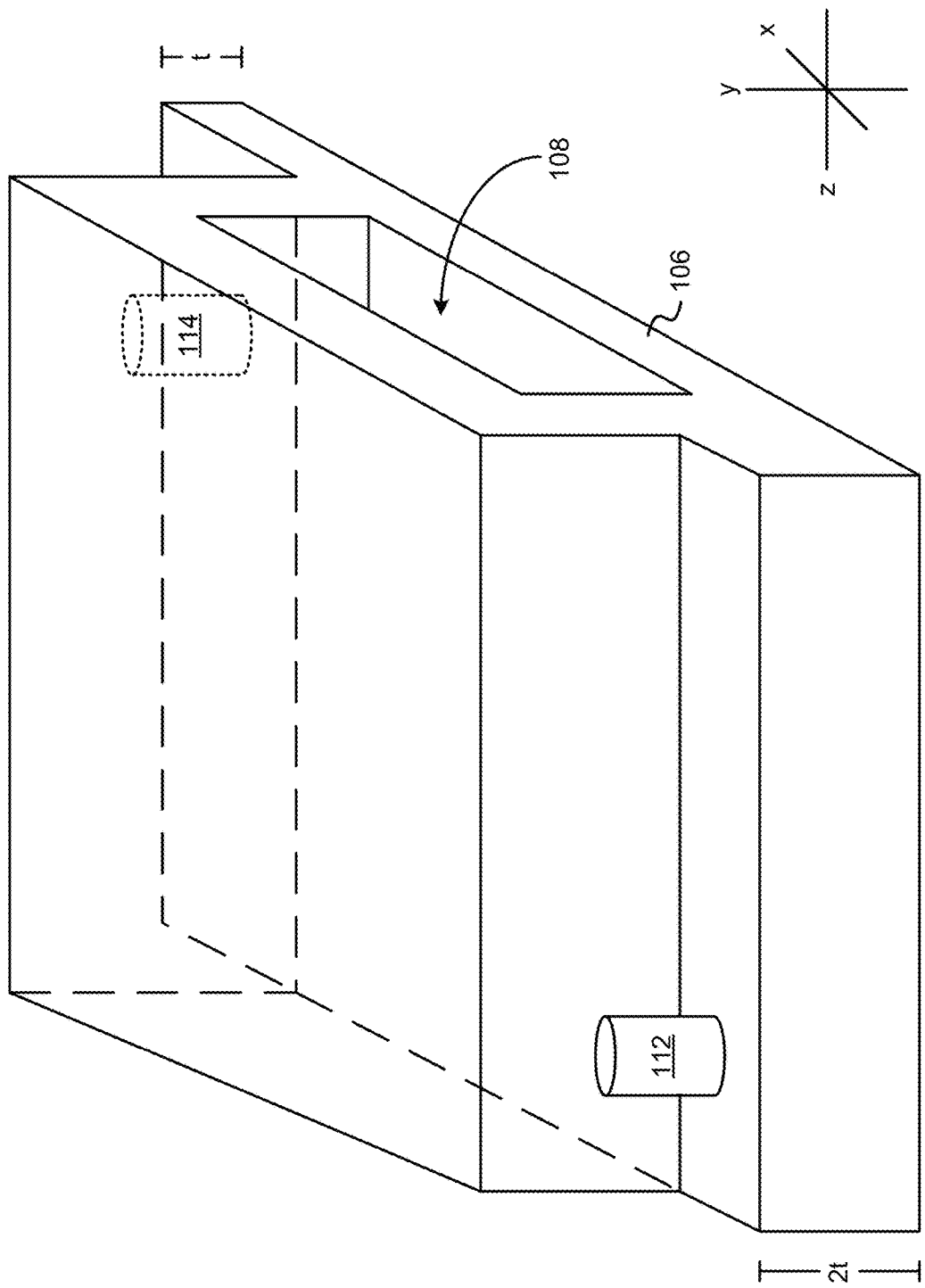

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

The following description discloses several preferred embodiments of in-vitro tissue bioreactors and/or related methods.

The presently disclosed technology demonstrates a novel system that combines primary or stem cell derived human or animal cells, tissue engineering, integrated sensors and diagnostics, integrated environmental controls, and novel fluidics, creating an in-vitro platform to reproduce in-vivo physiological response to study the effects of exposure to stresses such as drugs, toxins, adverse environmental conditions, pathogens, abnormal tissues such as cancer, nutrient depravation, etc. as would be understood by one having ordinary skill in the art upon reading the present descriptions. In various approaches, cell types usable with the presently disclosed systems may include any type of cells, e.g. primary, iPS derived stem cells, embryonic, progenitor cells, etc.

Also, in preferred embodiments the individual system components will be connected in a physiological manner so that the in-vitro system will recapitulate the in-vivo system in a physiologically relevant manner.

This platform provides a highly-integrated, multi-organ, human-relevant tissue reactor for rapidly assessing and predicting the toxicity, safety and efficacy of new drug entities in order to accelerate both development and regulatory approval of medical products, especially medical countermeasures against chemical, biological, and radiological (CBR) agents. This platform also provides the ability research and understand host-pathogen reactions on human tissue and organ systems in a manner not previously possible. For example, this platform can be used to study the evolution of zoonotic development of emerging viruses such as the bird flu (H5N1).

The technology demonstrates an assembly of computer-controlled reactors designed to support living human cells and tissues enabling precise control of environmental conditions to maintain long-term cell functionality, imaging, real time stimulation and recording with electrophysiological multi-sensor arrays, and real time biochemical sensing.

The technology takes the form of an integrated platform for long-term vitality, functionality and in vitro analysis of human tissue, featuring: electrical stimulation and recording of primary human cells, nutrient and oxygen perfusion via controlled delivery, temperature and gas control, chemical sensing, electrochemical and mechanochemical sensing, and allows optical analysis of cell adhesion, growth and functionality.

This integrated platform includes technology that enables researchers to rapidly and accurately prioritize new drugs for animal and human testing as well as study host and pathogen interactions, and behavior of abnormal tissues and organs. This advancement could shorten the development time of pharmaceuticals by an estimated 50% and reduce the cost of human clinical trials through earlier selection of winning therapeutic candidates, in addition to providing more realistic models for clinical trials, potentially reducing the occurrence of unanticipated adverse effects and negative consequences associated therewith.

In one general embodiment, a system includes a bioreactor coupled to a substrate. The bioreactor includes: a plurality of walls defining a reservoir; a plurality of fluidic channels in at least some of the walls; a fluidic inlet in fluidic communication with the reservoir via the fluidic channels; a fluidic outlet in fluidic communication with the reservoir via the fluidic channels; and one or more sensors coupled to the reservoir, each sensor being configured to detect one or more of: environmental conditions in the reservoir; and physiological conditions of one or more cells optionally present in the reservoir.

In another general embodiment, a method includes delivering media to a reservoir of a bioreactor; delivering a plurality of cells to the reservoir, wherein at least some of the cells are disposed onto one or more sensors in the bioreactor; controlling a reservoir temperature and a reservoir gas composition; using one or more of the sensors to monitor one or more of: environmental conditions in the reservoir, and physiological conditions of at least some of the cells; and communicating the monitored environmental conditions and/or physiological conditions to an external device.

To provide context for understanding the various functionalities of the presently disclosed inventive embodiments, these descriptions will be made primarily with reference to neural tissue cells, and particularly dorsal root ganglia neurons. However, those having ordinary skill in the art of microbiology will appreciate that the principles discussed herein may be equally applied to a broad variety of cell and tissue types, such as central nervous system tissue cells, cardiovascular tissue cells, pulmonary tissue cells, hepatic tissue cells, gastrointestinal tissue cells, connective tissue cells, hematological tissue cells, endocrinological tissue cells, etc.

Dorsal root ganglia neurons are the cell bodies of sensory neurons whose axonal nerve endings are located in the skin, muscles, tendons, joints and internal organs. These neurons have a variety of sensory receptors that are activated by mechanical, thermal, chemical, and noxious stimuli, making them an excellent model system for studying the neurotoxic effects of chemicals in vitro. Changes in electrophysiology, ion channel function, morphological characteristics, and neurite growth parameters have been used to understand the effects of toxic agents on the ganglia.

Preferably, the present systems and techniques may be utilized to enable and facilitate study of physiologically relevant systems comprising tissues, organs, etc. singly and/or in combination according to an arrangement or configuration that substantially represents or replicates all the essential features, forms, and functions of a corresponding tissue, organ, or combination thereof. For example, in one approach a physiologically-relevant vasculature (including a variety of vessel types characterized by a range of diameters from the capillary scale to the arterial/venous scale, branching according to a three-dimensional network representing a bifurcating structure with channels that progressively narrow with increasing bifurcation (i.e. each "branch" sprouts from a relatively larger "trunk" as measured with respect to interior and/or exterior diameter), inter-branch spacing of no greater than about 200 microns, etc. as would be understood by one having ordinary skill in the art upon reading the present descriptions.

However, conventional neurotoxicology techniques traditionally employed to monitor such changes are unfavorable, because these techniques (such as cellular assays) use time consuming and laborious methods that interrogate one cell at a time. By contrast, the presently disclosed technology enables interrogation of single cells or simultaneous interrogation of many cells (on the order of $10^2$ cells, in some approaches) using efficient methods.

Various embodiments of the presently disclosed inventive concepts will now be described with reference to the Figures. As will be appreciated by one having ordinary skill in the an upon reading the present descriptions, the illustrative embodiments depicted in the Figures and described below are provided by way of example only, and are not intended to be limiting on the scope of the disclosed inventive concepts.

Bioreactor

As shown in FIG. 1, a system 100 includes a bioreactor 102 coupled to a substrate 104. Preferably, the substrate 104 is optically transparent. The bioreactor 102 includes: a plurality of walls 106 defining a reservoir 108. The walls 106 have fluidic channels 110 embedded therein to facilitate introducing, evacuating and/or mixing various fluids in the reservoir 108. A fluidic inlet 112 engages a port in the walls 106 to facilitate fluidic communication with the reservoir 108 via the fluidic channels 110. Similarly, a fluidic outlet 114 engages a port in the walls 106 to facilitate fluidic communication with the reservoir 108 via the fluidic channels 110. In one approach, fluid traverses the reservoir 108 generally in the direction indicated by the arrow depicted in the reservoir 108, i.e. in a substantially left-to-right direction according to the view depicted in FIG. 1. Of course, the fluid may move around in the reservoir 108 in any direction, but the fluid may be characterized by a net motion substantially in the direction indicated in FIG. 1.

In various approaches, the bioreactor system as shown in FIG. 1 may be configured such that the external dimensions thereof are substantially similar to those commonly found in plates utilized for standard cell culture, microbiology and/or molecular biology applications. This may also be expressed as the device being configured in a "standard well format" such as a traditional 96-, 48-, 24-well plate, etc. or any other standard format known in the art. Advantageously, this standard configuration enables the system to be utilized in combination with existing high-throughput instrumentation and automated instrumentation, allowing users to leverage all the optical and robotic processes the industry has developed.

One or more sensors 116 are arranged in the reservoir 108, preferably in an ordered array configured to facilitate the sensors 116 engaging cells 120 optionally present in the reservoir 108. Each sensor 116 is configured to detect one or more of: environmental conditions in the reservoir 108; chemical conditions of a fluid 118 optionally present in the reservoir 108, and physiological conditions of one or more cells 120 optionally present in the reservoir 108.

The sensors 116 are preferably connected to electrical interconnect pads 122 via a trace metal such as platinum, copper, etc., as will be discussed in further detail below with further reference to FIG. 3. Additionally and/or alternatively, one or more interconnect pads 122 may be positioned on the substrate 104 and configured to communicate data between the bioreactor 102 and a processor (e.g. via conductive paths such as printed circuitry on the substrate 104 and/or a detachable control board such as described in further detail below with respect to FIGS. 3 and 7).

An enclosure 124 separates the bioreactor components discussed above from the ambient environment, in some approaches. The enclosure 124 is preferably an optically transparent material, and optionally includes a temperature control mechanism 126 configured to regulate temperature of the bioreactor environment, for example to maintain human physiological temperature in the reservoir 108. The enclosure 124 is coupled to the substrate 104, and the coupled substrate 104 and bioreactor 102 may be additionally coupled to one or more support structures 128 in some embodiments.

For example, in one embodiment the support structures 128 may include a polymer-based support structure 128, and may include printed circuitry such as described in further detail below with respect to FIGS. 3 and 6. The support structures 128 may alternatively be a base plate assembly such as described below in further detail with respect to FIG. 5, mounting platform of an imaging device, such as an optical, fluorescent, or other microscope, a mounted CCD camera, etc. in various approaches.

In more embodiments, the system includes a bioreactor 102 coupled to a composite substrate 104. The composite substrate 104 comprises a glass portion and polymer portion. The glass portion may include an optically transparent material such as borosilicate, Pyrex, Kimax, soda lime glass, an optically transparent polymer, etc. as would be understood by one having ordinary skill in the art upon reading the present descriptions. The polymer portion of the substrate 104 may include a material such as an acrylic resin, polyimides, parylene, polystyrene, silicon oxide, silicon dioxide, silicon nitride, silicone, a dielectric compound or structure, etc. as would be understood by one having ordinary skill in the art upon reading the present descriptions.

Moreover, the polymer portion of the substrate 104 preferably has an optically transparent viewing window (e.g. a port positioned between support structures 128 as shown in FIG. 1, according to one embodiment). The window may be adapted to enable easy observation and collection of optical information from the reservoir 108. Optical information may include any data suitable for characterization of cell adhesion, growth and/or functionality, such as cell length along a given dimension or axis, cell morphology, cell density, cell surface area/volume, etc. as would be understood by one having ordinary skill in the art upon reading the present descriptions.

The bioreactor 102 includes an enclosure 124 enclosing a reservoir 108. The reservoir 108 is defined by a plurality of walls 106, which are preferably optically transparent and may include materials such as those disclosed immediately above regarding the polymer portion of the substrate 104. Furthermore, at least some of the walls 106 include a plurality of fluidic channels 110 and/or gas exchange channels 130, which have dimensions suitable for conducting fluid and/or gases between the reservoir 108 and one or more other reservoirs 108 containing media, experimental reagents, carbon dioxide gas, oxygen gas, waste, etc. as would be understood by one having ordinary skill in the art upon reading the present descriptions. The fluidic and/or gas-exchange channels 110, 130 may have a width and/or a height in a range of about 100 μm to 400 μm, but could be higher or lower depending on the embodiment. In one preferred embodiment, the fluidic channels 110 have a width of about 250 μm and a height of about 250 μm to facilitate fluidic communication with the reservoir 108 via, the fluidic inlet 112 and/or the fluidic outlet 114. The various channels referred to herein will be described in further detail below with reference to FIGS. 4A-4D, according to several exemplary embodiments.

The reservoir 108 also includes one or more sensors 116, which may include electrodes (or "electrical sensors") in some embodiments, such as shown in FIGS. 1-3 and 7 and described in further detail below. Each sensor 116 is preferably configured to detect one or more of: environmental conditions in the reservoir 108 and physiological conditions of one or more cells 120 present in the reservoir 108.

In other embodiments, the bioreactor 102 platform may include a single reservoir 108 and a surface-mounted omnetics connector, as depicted in the figure immediately below. This configuration may have 16 fluidic channels, but cannot be autoclaved without detrimentally affecting the surface mounted omnetics connector, and thus may be sterilized using other means, such as with ethylene oxide. As will be further appreciated by those having ordinary skill in the art upon reading the present descriptions, the bioreactor 102 system disclosed herein may, in some embodiments, include a plurality of bioreactors 102 on a single assembly platform, as shown above. This capability enables performing multiple experiments simultaneously and performing multiple replicates of an experiment to gather more robust data, among other advantages.

In some approaches, various tissue types may be plated and monitored in independent or interconnected reservoirs 108 on the same platform. The fluidic configuration can be customized to allow physiological interaction between these reservoirs 108 to understand the relationship between different tissue types, as would be understood by one having ordinary skill in the art upon reading this disclosure.

In more approaches, a single bioreactor 102 may house a plurality of reservoirs 108 or "wells," much as the exemplary arrangement shown below, which includes 8 distinct wells in a single bioreactor 102 platform. The wells are each controlled independently with respect to environmental conditions (e.g. temperature, gas composition) delivery of fluids, and use of the sensors to stimulate cells, record experimental data, etc. This configuration advantageously allows simultaneous replication of experiments on a single platform to minimize extraneous variables and generate robust data for subsequent analysis.

One particularly advantageous feature of the presently disclosed bioreactor 102 platforms is that the bioreactors 102 and platforms have a miniaturized footprint. Notably, the entire system is substantially similar in width and depth to that of standard 96-well or 384-well plates typically used in a variety of microbiological, biochemical, and related applications. This enables the miniaturized in-vitro tissue bioreactor platform to be seamlessly used and integrated with a wide variety of existing and industry-standard instrumentation and technology, such as robotic liquid handling platforms, autoclaves, imaging systems, cell culture instrumentation and/or systems, etc. as would be understood by one having ordinary skill in the art upon reading the present descriptions.

Figure 7:
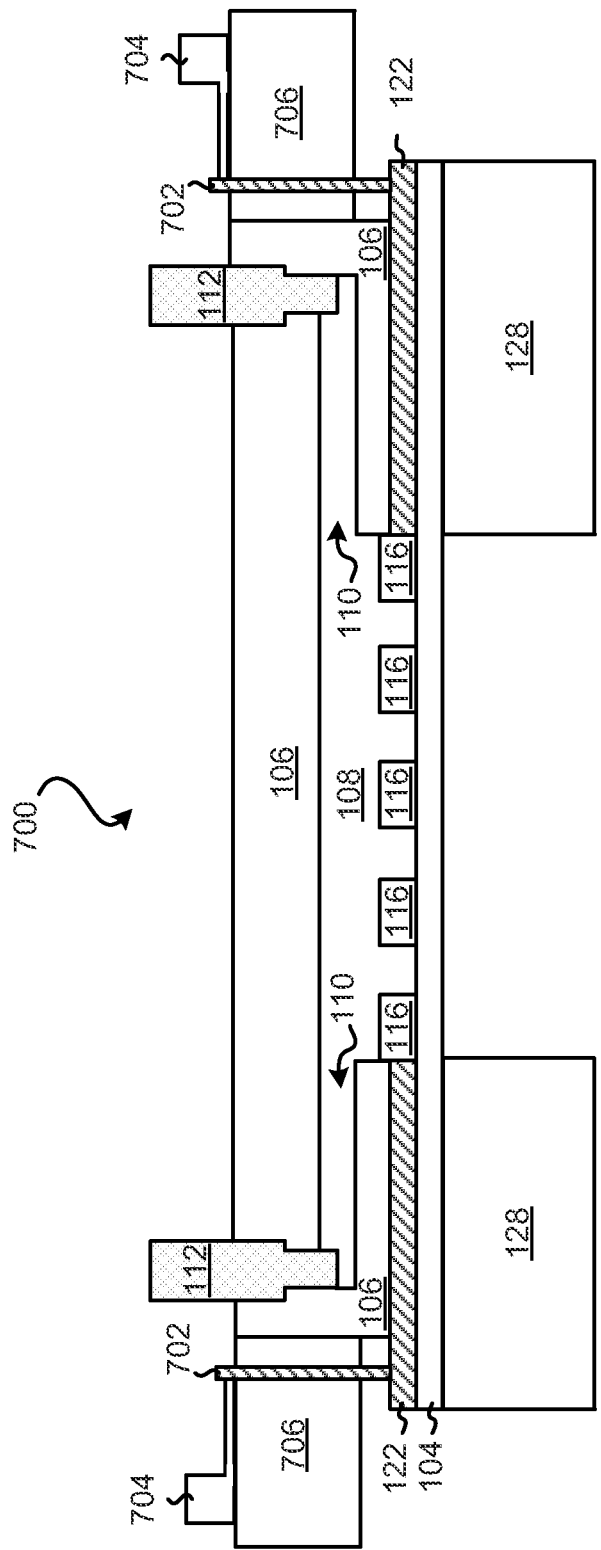
FIG. 7 shows a simplified side-view schematic of an assembled bioreactor platform including a bioreactor with a closed-top configuration, a control board, and a communication interface, according to one embodiment.

In a preferred embodiment, the system has a width no greater than approximately 125 mm (e.g. 125±5 mm) and a depth no greater than approximately 82.5 mm (e.g. 82.5±5 mm). Of course, other dimensions are fully within the scope of the present disclosures, as will be appreciated by one having ordinary skill in the art upon reading the present descriptions. For example, some embodiments may have dimensions up to 2 or 3 times the aforementioned dimensions. An exemplary illustration of the platform assembly to which the remainder of the bioreactor 102 is coupled is shown in FIG. 7, according to one embodiment.

In various approaches, the bioreactor 102 platform may be positioned in proximity to an imaging device such as a CCD camera, a microscope (which may be a bright-field microscope, fluorescent microscope, electron microscope, etc.), or other imaging device known in the art and usable to image the cells 120 in the reservoir 108. The imaging device may be placed in any position relative to the bioreactor 102 that affords a line of sight into the bioreactor 102 reservoir 108. The imaging device may be located, for example, below the bioreactor 102 and have a line of sight into the reservoir 108 via the optical viewing window (i.e. through the glass substrate 104), above the bioreactor 102 and have a line of sight into the reservoir 108 via the optically transparent walls 106 of the bioreactor 102, etc., in various approaches.

Reservoir Configuration

Several exemplary embodiments of a reservoir 108 configuration within the scope of the present disclosures will now be detailed. Those having ordinary skill in the art will appreciate that the present descriptions are offered by way of illustration only and are not intended to be limiting on the scope of the instant disclosures.

In various approaches, the bioreactor 102 may have a reservoir 108 characterized by either an enclosed-top or an open-top, and may additionally and/or alternatively include gas-exchange channels in either configuration, as shown according to several exemplary embodiments in FIGS. 2A-2E.

Figure 2A:
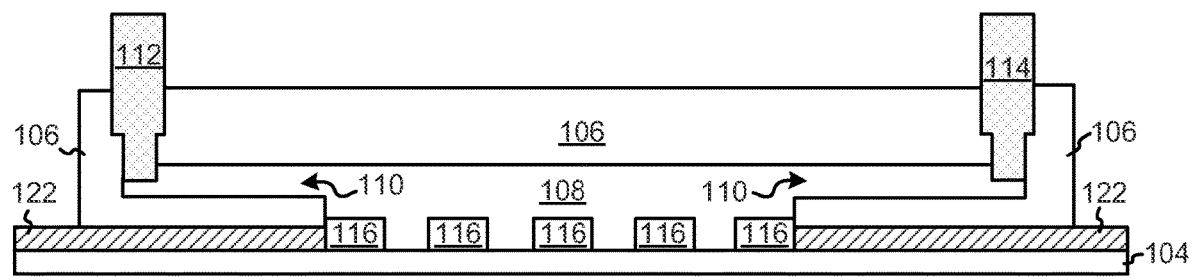
FIG. 2A depicts a side view of a simplified schematic of a bioreactor having a closed-top configuration, according to one embodiment.

As shown in FIG. 2A, in one embodiment a bioreactor features a closed-top configuration having a reservoir 108 defined by a plurality of walls 106 as described generally above regarding FIG. 1. When viewed from the side, such as according to the perspective shown in FIG. 2A, the reservoir 108 is enclosed by side walls 106 and an upper wall 106, The upper wall 106 has disposed therein an inlet valve 112 and outlet valve 114, each being configured to engage a fluidic system and facilitate delivery and/or removal of various materials to and from the reservoir 108, in one embodiment. Preferably, the side walls 106 and upper wall 106 are configured to form channels 110 in the reservoir 108 to facilitate introduction of materials via the inlet valve 112 and/or evacuation of materials via the outlet valve 114.

As shown in FIG. 2A, the exemplary closed-top reservoir configuration also includes a plurality of sensors 116 disposed in the reservoir 108, as well as one or more interconnect pads 122. The interconnect pads 122 are preferably positioned vertically between the side walls 106 and a substrate 104 upon which the remainder of the bioreactor assembly rests, according to the perspective depicted in FIG. 2A. Of course, alternative arrangements and/or configurations that would be appreciated by a skilled artisan upon reading the instant descriptions are also fully within the scope of the presently disclosed embodiments.

Figure 2B:
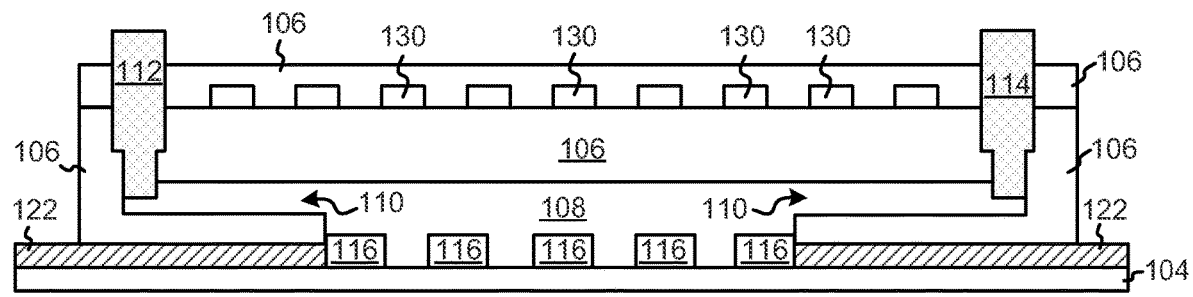
FIG. 2B depicts a side view of a simplified schematic of a bioreactor having a closed-top configuration and a plurality of gas-exchange channels, according to one embodiment.

In more embodiments, such as shown particularly in FIG. 2B, the configuration described above with reference to FIG. 2A may additionally include a plurality of gas-exchange channels 130. In one approach, the gas exchange channels 130 may be formed in one or more of the walls 106, preferably at least the upper wall 106, such as depicted in FIG. 2B. Additionally and/or alternatively, the gas exchange channels 130 may be formed in an additional layer disposed above the upper wall 106 (which may be refer d to as a "capping layer" in some approaches). The capping layer 106 may be formed from the same material as other walls 106, in preferred approaches.

Figure 2C:
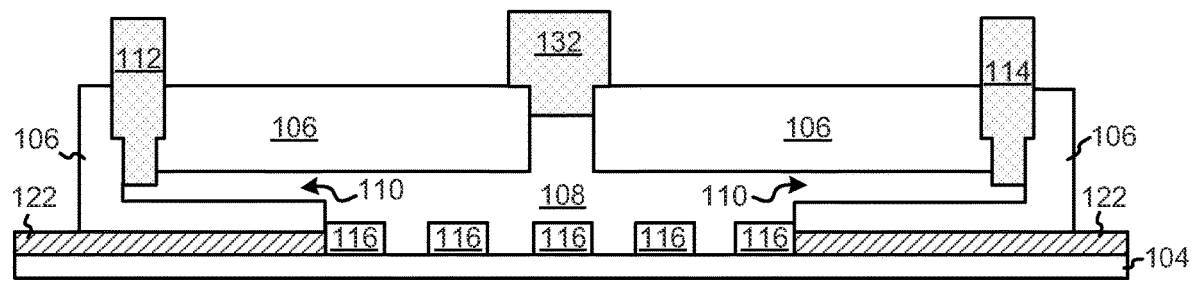
FIG. 2C depicts a side view of a simplified schematic of a bioreactor having an open-top configuration, according to one embodiment.

By contrast, and as shown according to one embodiment in FIG. 2C, the presently disclosed bioreactors may employ reservoir(s) 108 having an open-top configuration. The open-top configuration is preferably substantially identical to the closed-top configuration shown in FIG. 2A, with the exception that upper wall 106 includes an aperture or opening configured to facilitate introducing and/or evacuating materials to and/or from the reservoir 108. As shown in FIG. 2C, the aperture is located in an approximately central horizontal position with respect to the upper wall 106, effectively dividing the upper wall 106 into two horizontal sections as viewed from a side perspective such as in FIG. 2C. The aperture need not occupy an entire depth of the upper wall 106 according to the perspective shown in FIG. 2C, but may rather preferably form a "hole" in the upper wall 106 configured to engage one or more cell-culture tools such as a serological pipette, a micropipette, a fluidics system interface, etc. as would be understood by one having ordinary skill in the art upon reading the present descriptions. Preferably, the aperture is also configured to be removably sealed by a plug 132 such as a septa plug, in some approaches.

As shown particularly in FIG. 2D, the open-top configuration may additionally and/or alternatively include a plurality of gas exchange channels 130 in a manner substantially similar to that described above regarding FIG. 2B. Preferably, the aperture is configured to allow access through the upper wall 106 and/or capping layer 106 to the reservoir 108, e.g. via one or more of the cell-culture tools referenced above. According to this (preferred approach, in some embodiments both the upper wall 106 and capping layer 106 may be effectively divided into two horizontal sections according to a side view perspective such as shown in FIG. 2D. The open-top configuration including gas exchange channels 130 depicted in FIG. 2D may otherwise be substantially identical to the closed-top configuration including gas channels 130 depicted in FIG. 2B, in some approaches.

Each configuration confers unique advantages, in various embodiments. For example, in one approach the closed-top configuration advantageously reduces the risk of contamination from the environment or users of the bioreactor 102, because the bioreactor 102 may be sterilized and subsequently populated with requisite reagents and/or cells for a desired study, connected to an automated or semi-automated fluidic system, and observed over the course of an experiment without further risk of contamination (e.g. by opening or otherwise exposing the reservoir 108 and/or various channels coupled to the reservoir 108 to an unsterilized sterile environment).

Meanwhile, the open-top configuration advantageously provides the ability to access the reservoir 108 directly without resorting to the fluidics systems discussed above. This direct access may advantageously reduce loss of cells 120 or other reagents compared in other delivery methods using the incorporated fluidics. This design is also configured to reduce the shear stress applied to sensitive cells 120 during introduction into the reservoir 108. Fluids flowing through the fluidic channel 110 may, in some applications, apply undesirably high shear stresses to cells, which in extreme cases may cause the cells to become unhealthy or die, defeating any subsequent ability to conduct meaningful experimentation/observation thereof.

The openings in the open-top and/or closed-top configurations may be adapted to be removably sealed by septa plugs, in some approaches. The septa plugs may preferably seal the open reservoir 108 during incubation duce evaporation of fluid/media from the chambers and inlet/outlet ports 112, 114. Even more preferably, septa plugs contemplated for use in conjunction with the presently described systems are configured to facilitate selective exchange and/or transfer of gases, liquids, and/or particles between the bioreactor environment and an ambient environment, container, reservoir, etc. to which the bioreactor is coupled, e.g. via fluidics.

The open-top configuration shown above may also be combined with including a plurality of gas-exchange channels 110 in the walls 106 of the reservoir 108 to facilitate con oiling the gas composition of the reservoir 108 environment. A side-view of an open-top configuration including such gas-exchange channels 110 is shown below, according to one exemplary embodiment.

In other embodiments, such as shown in FIG. 2E, the substrate 104 may include a plurality of vacuum channels 134 configured to facilitate applying a light vacuum to the reservoir 108 in order to attract cells 120 toward the viewing window and/or sensors 116, thereby enhancing observation of the cells 120 and the cells' characteristics (observed via the sensors 116, e.g. observed electrical recordings in the form of action potentials). In more embodiments, the sensors may optionally be functionalized to read chemical signatures for one or more target molecules in real time, such as dopamine, acetylcholine, gamma-aminubutyric acid (GABA), and/or other chemical and/or biochemical markers that would be appreciated by one having ordinary skill in the art upon reading the present descriptions.

As will be understood by those having ordinary skill in the art upon reading the present descriptions, the various configurations depicted in FIGS. 2A-2E are to be considered as modular features which may be employed in any rational combination in various embodiments of the bioreactor systems disclosed herein. For example, a bioreactor within the context of these disclosures may include an open-top or closed-top configuration interchangeably in combination with gas exchange channels 130 and/or vacuum channels 134. The sole limitation on such combinations is that a single bioreactor cannot simultaneously have an open-top and a closed-top configuration (although systems disclosed herein that include multiple bioreactors, such as described in further detail below, may include bioreactors having a closed-top configuration and bioreactors having an open-top configuration, in some approaches).

Sensors/Sensor Array

The sensors 116 will now be described in further detail with reference to FIGS. 1-3, according to several illustrative approaches.

In various approaches, sensors 116 may be arranged in an organized structure, such as a ring to facilitate simultaneous stimulation and viewing of cells, a nanowire to stimulate and/or monitor three-dimensional cellular structures like an extra-cellular matrix (ECM) or three-dimensional organ, organ scaffold, tissue construct, etc. as would be understood by one having ordinary skill in the art upon reading the present descriptions.

Optionally, the sensors 116 may be configured to facilitate the cells 120 being or becoming positioned in gaps between the sensors 116 so as to best enable optical observation of the cells 120, e.g. from above, from the side, or from underneath via a viewing port in the substrate 104 (e.g. a region between support structures 128). In additional and/or alternative arrangements, the sensors 116 may be configured to facilitate cells 120 being or becoming positioned on or within an area occupied by the sensor 116. For example, the sensors 116 may be configured as ring-like structures to encourage cells 120 nestling in a central region (i.e. interior to the ring) to facilitate optical observation of the cell white also maintaining conditions (e.g. spatial proximity, electrical coupling, chemical coupling, etc. as would be understood by one having ordinary skill in the art upon reading the present descriptions) sufficient to detect and/or monitor physiological characteristics of the cell 120 and/or physiological processes Ongoing within the cell 120.

In some approaches, particularly where sensors are arranged in ring structures, each electrode may be characterized by a diameter in a range from about 30 μm and about 90 μm, but could be larger or smaller. Furthermore, if multiple sensors are present, the sensors may be arranged in a common plane along the bottom (viewing) surface of the reservoir 108, and the sensors are separated from one another in the plane by about 100 μm to about 500 μm, e.g., 200 μm, i.e. the sensors are characterized by a 100-500 μm spacing therebetween.

In some embodiments, functionalized self-assembled monolayers may be selectively patterned onto the electrode surface to enhance single-cell adhesion to individual sensors. Cells 120 such as dorsal root ganglions (DRGs) be dispersed onto the electrode array, and spatially integrated within the native extracellular matrix (ECM) for physiological support and structural integrity. Non-invasive single cell recording and stimulation may be facilitated using suitable equipment known in the art, such as a PAR potentiostat.

Electrode and/or sensors 116 may be functionalized, in some embodiments, to facilitate cell adhesion to the sensors, to detect the presence of chemicals of interest in the reservoir 108, to detect environmental conditions in the reservoir 108, to detect physiological changes in the cells, etc. as would be understood by one having ordinary skill in the art upon reading the present descriptions.

For example, in some embodiments surface functionalization may include modifications for dopamine sensors 116. In other embodiments, surface functionalization may enable monitoring of conditions such as such as pH, presence of chemicals of interest (e.g. metabolic agents, hormones, drugs, toxins, etc.), presence of biological markers, indicators of oxidative stress (e.g. lactate, pyruvates, etc.), indicators of cytotoxicity (e.g. nitric oxide), presence of neurotransmitters (e.g. acetocholine, glutamate, gamma aminobutyric acid (GABA), etc.) presence of one or more sequences of interest (e.g. DNA, mRNA, etc.), osmolarity of a solution in the reservoir 108, contractility of cells, etc. as would be understood by one having ordinary skill in the art upon reading the present descriptions.

The reservoir 108 may include various types and numbers of sensors 116, such as chemical sensors, electrical sensors, thermal sensors, etc. as would be understood by one having ordinary skill in the art upon reading the present descriptions. Preferably, the sensor(s) 116 are configured to detect and/or observe one or more phenomena and/or collect data relating thereto.

For example, the sensors 116 in one embodiment may include one or more of electrical sensors configured to detect one or more electrical conditions, such as an electrical potential across a cell or population of cells; optical sensors configured to detect one or more optical phenomena such as an amount of light present/emitted within the reservoir 108 (e.g. light of a particular wavelength being emitted by one or more cells, such as in a fluorescent in-situ hybridization experiment); chemical sensors configured to detect chemical conditions in the reservoir 108 such as presence and/or concentration of a target compound or compounds (including biological molecules such as the indicators, markers, an neurotransmitters described above, gases such as carbon monoxide, carbon dioxide, oxygen, nitrogen, etc. as would be understood by one having ordinary skill in the art), pH, etc.; mechanical sensors 116 configured to detect one or more mechanical forces acting on contents of the reservoir 108 (e.g. physical strain on cells, e.g. shear stress, surface tension, etc.), thermal sensors configured to detect an environmental temperature in one or more regions of the bioreactor (e.g. in the enclosure 124, in the walls 106, in the reservoir 108, etc.). Any combination of the aforementioned sensors 116 and/or sensor functionalities may be utilized, in various embodiments.

In even more embodiments, the sensors 116 may be formed in whole or in part from a material selected from the group consisting of: platinum, indium oxide, gold and activated iridium oxide. In some approaches, a single sensor 116 may be configured to detect chemical conditions in the reservoir 108, mechanical forces acting on contents of the reservoir 108 and stimulate cells 120 with electrical impulses, as well as any other functionality described herein.

The sensors 116, particularly sensors 116 comprising electrodes, may be formed of any suitable conductive material, and are preferably formed of optically transparent, biologically-inert conductive materials. For example, sensors may include materials such as thin-film or electroplated platinum, thin-film activated iridium oxide, thin-film gold, indium oxide, etc. as would be understood by one having ordinary skill in the art upon reading the present descriptions.

Sensors 116 may be arranged throughout the reservoir 108, and in one embodiment may be arranged in an array or matrix along a reservoir surface closest to the optical viewing window in the substrate 104. A top-down view of one embodiment of such an exemplary sensor arrangement 300 is shown in FIG. 3, according to one embodiment.

Figure 3:
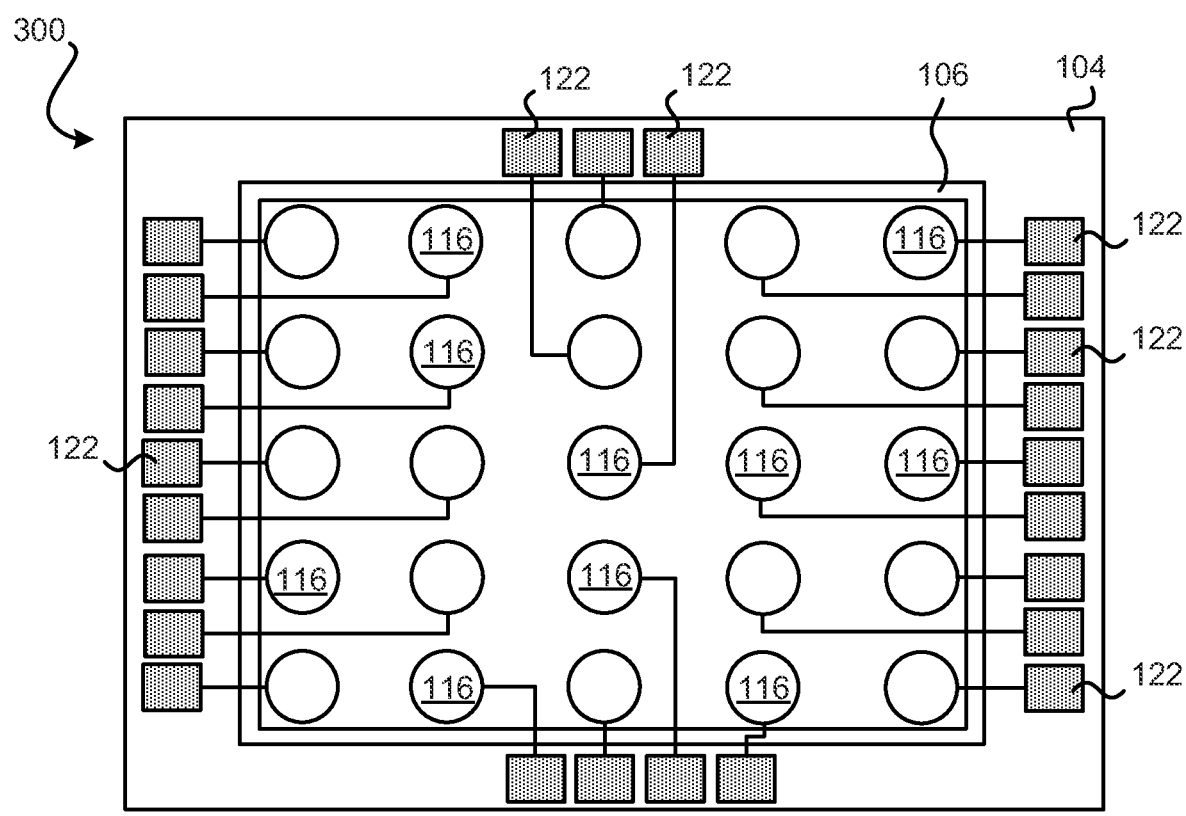
FIG. 3 depicts a simplified schematic of a sensor array shown from a top-down view, according to one embodiment.

As shown in FIG. 3, an exemplary sensor arrangement 300 includes a substrate 104 having disposed thereon one or more walls 106 such as described above with reference to FIGS. 1-2E. The arrangement 300 also includes a plurality of sensors 116 and interconnect pads 122 disposed in and/or on the substrate 104. In preferred embodiments, the interconnect pads are arranged around a periphery of the substrate 104 in a manner configured to facilitate one or more portions of the arrangement 300 being engaged by a communication interface (also referred to as an "electrical connector") such as an omnetics connector (e.g. as shown and described below with reference to FIG. 7) to enable communication between configured to facilitate communicating operational instructions and/or experimental data between an external device to which a bioreactor 102 is coupled and the various components of the reactor itself (such as the sensors 116 of sensor arrangement 300 shown in FIG. 3, fluidic systems shown in FIGS. 1-2E, and 4A-4E, heating elements, etc. as would be understood by one having ordinary skill in the art upon reading the present descriptions).

The sensors 116 and/or interconnect pads 122 preferably comprise a conductive material, more preferably a metal, and even more preferably a trace metal such as platinum, gold, indium oxide, or other material described herein as suitable for use in the sensor(s) 116, in various approaches.

With continuing reference to FIG. 3, each sensor 116 is preferably coupled to at least one interconnect pad 122, and more preferably to exactly one interconnect pad 122 via a conductive path (indicated in FIG. 3 by a line connecting each sensor 116 with an interconnect pad 122). The conductive path, in various embodiments, may take the form of a wire disposed in and/or on the substrate 104, a printed circuit formed in and/or on the substrate 104, or any other suitable conductive material and/or coupling capable of being affected between a sensor 116 and an interconnect pad or pads 122 as would be understood by one having ordinary skill in the art upon reading the present descriptions.

Sensor Array Fabrication

In one embodiment, the sensors/sensor array, optionally including corresponding interconnect circuitry and/or interconnect pads 122 may be fabricated according to a general process as described and shown in FIGS. 8A-8E, in one approach.

Figure 8A:
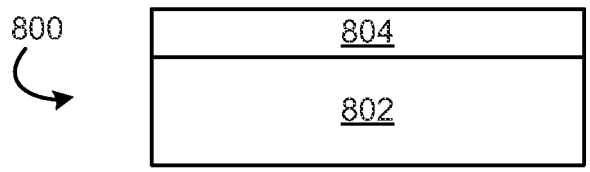
FIGS. 8A-8E depict simplified side-view schematics of a bioreactor sensor array in various stages of a production method, according to one embodiment.

A first fabrication operation may include depositing a first polymer layer 804 on a substrate 802 to form a structure 800 substantially as shown in FIG. 8A, in one approach.

Figure 8B:
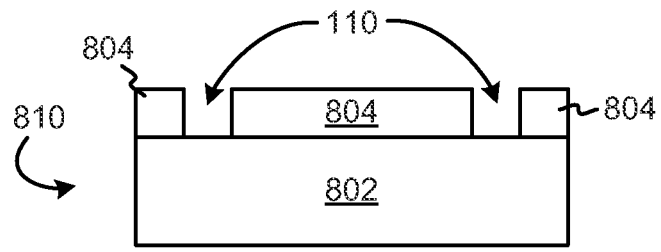

In another approach, a second fabrication operation may include etching channels in the first polymer layer 804 to form a structure 810 substantially as shown in FIG. 8B. In some approaches, the channels may have a width and/or height (depth) in a range from approximately 100 µm to approximately 400 µm.

Figure 8C:
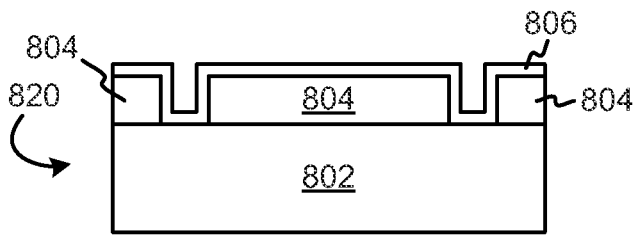

A third fabrication operation according to one embodiment may include depositing trace metal 806 (such as platinum and/or another metal discussed herein as suitable for use in the sensors 116) is deposited onto the etched polymer layer 804 to form a structure 820 substantially as shown in FIG. 8C.

Figure 8D:
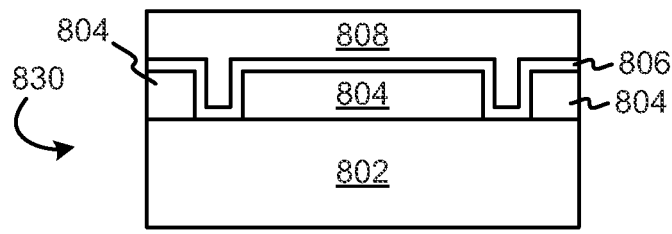

In another embodiment, a fourth fabrication operation includes depositing a second polymer layer 808 onto the deposited first polymer layer 804 and trace metal 806 to form a structure 830 substantially as shown in FIG. 8D.

Figure 8E:
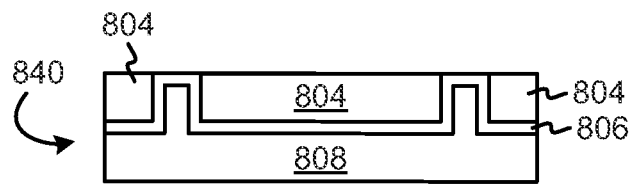

In a fifth fabrication operation, the assembled polymer layers and trace metal(s) may be released from the substrate 802 to obtain the sensor/electrode array 840 substantially as shown in FIG. 8E.

In more embodiments, the sensors/sensor array 116, optionally including corresponding interconnect circuitry and/or interconnect pads 122 may be fabricated according to a general process as described and shown in FIGS. 9A-9D.

Figure 9A:
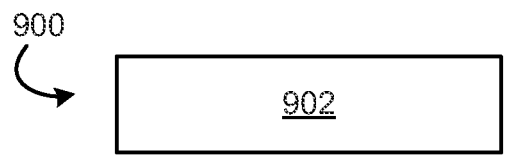
FIGS. 9A-9D depict simplified side-view schematics of a bioreactor sensor array in various stages of a production method, according to one embodiment.

The fabrication method may include a first fabrication operation, where a substrate 902 is provided substantially as shown in FIG. 9A. The substrate may comprise glass, a conductive polymer, an insulating polymer, or any other suitable material as described herein and/or would be appreciated by one having ordinary skill in the art upon reading the present descriptions. Providing the substrate 902 results in structure 900.

Figure 9B:
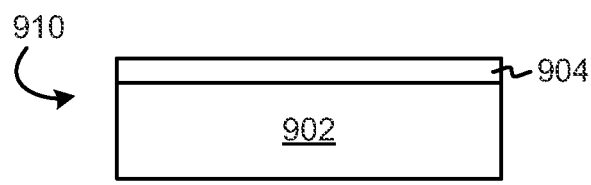

A second fabrication operation includes depositing a layer 904 comprising a metal on at least one surface of the substrate 902. The metal deposited in layer 904 preferably comprises a material disclosed herein as suitable for use in sensors/sensor array 116, such as a trace metal discussed above with reference to FIG. 8C. Depositing layer 904 produces a structure 910 as shown in FIG. 9B, in one approach.

Figure 9C:
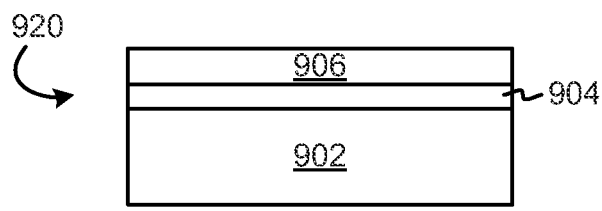

Proceeding to FIG. 9C, forming a polymer layer 906 on at least one surface of the metal layer 904 results in a structure 920 comprising the substrate 902, metal layer 904 deposited on the substrate 902, and a polymer layer 906 deposited on at least one surface of the metal layer 904, in one exemplary embodiment.

Figure 9D:
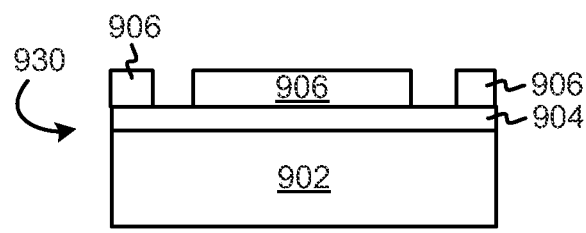

The presently disclosed fabrication method may also include, according to some approaches, etching channels in the polymer layer 906 to form a structure 930 substantially as shown in FIG. 9D. In some approaches, the channels may have a width and or height (depth) in a range from approximately 100 µm to approximately 400 µm. The resulting structure 930 may be utilized in functioning bioreactors such as described herein, and the use thereof may include exposing portions of the metal layer 904 exposed by etching the channels in the polymer layer 906 to cells, e.g. cells 120 as shown above in FIG. 1.

Fluidics/Channels

The bioreactor 102 fluidics will now be detailed with reference to several exemplary embodiments as shown in FIGS. 4A-4D. These descriptions and figures are not to be considered limiting on the scope of the instant disclosure, but rather are provided for illustrative purposes to facilitate fuller understanding of the presently described inventive concepts.

In one embodiment, illustrated by the top-down view of a bioreactor 102 fluidic channel 110 arrangement shown in the figure below, each bioreactor 102 reservoir 108 includes a plurality of fluidic channels 110 configured to deliver and/or remove various fluids and/or materials from the bioreactor 102 reservoir 108. The fluids and/or materials may be delivered to or from one or more reservoirs 108, using any suitable propulsion means, such as a syringe pump or Flo Pro, in one embodiment. Additionally and/or alternatively, various fluids may be delivered to and/or removed from the reservoir 108 using a syringe, pump, or any other suitable device as would be understood by one having ordinary skill in the art upon reading the present descriptions.

As shown below, the fluidic channels 110 include independent channels 110 for each of inputting media, cells, and assay reagents. The fluidics converge in the vicinity of the reservoir 108 to deliver the respective fluid to the reservoir 108 upon being pumped from a source container to the bioreactor 102 via a reservoir 108 inlet. Similarly, a reservoir 108 outlet 114 guides fluids in the reservoir 108 to one of a plurality of outputs via fluidic channels 110 as shown in the right side of the figure below. Gas exchange channels 110 such as the $CO_2$ channels 110 depicted in the schematic may facilitate transferring gasses between the bioreactor 102, one or more gas sources, and/or a waste outlet 114, in various approaches.

In a preferred embodiment, the reservoir 108 inlet(s) and outlet(s) 114 are physically arranged in a manner designed to facilitate mixing of fluids in the reservoir 108. For example, in one approach the reservoir 108 inlet(s) may be spatially offset from the reservoir 108 outlet(s) 114 in three dimensions (e.g. offset in all three of an x-coordinate, a y-coordinate and a z-coordinate). For example, if a reservoir inlet 112 is positioned at a top-left corner of a first wall 106 of the reservoir 108, the reservoir outlet 114 may be positioned at a bottom-left corner of a wall 106 opposite the first wall 106. The offset facilitates a vortex-effect forming in the reservoir 108 while pumping fluids into/out of the reservoir 108, thereby encouraging mixing of reservoir contents. Of course, other means of mixing (such as pumping fluids back and forth throughout the channels 110 and/or reservoir 108) are also within the scope of the instant disclosure. Advantageously, mixing helps to ensure uniform distribution of various compounds in the reservoir 108, such as media, drugs, toxins, waste, etc.

Figure 4A:
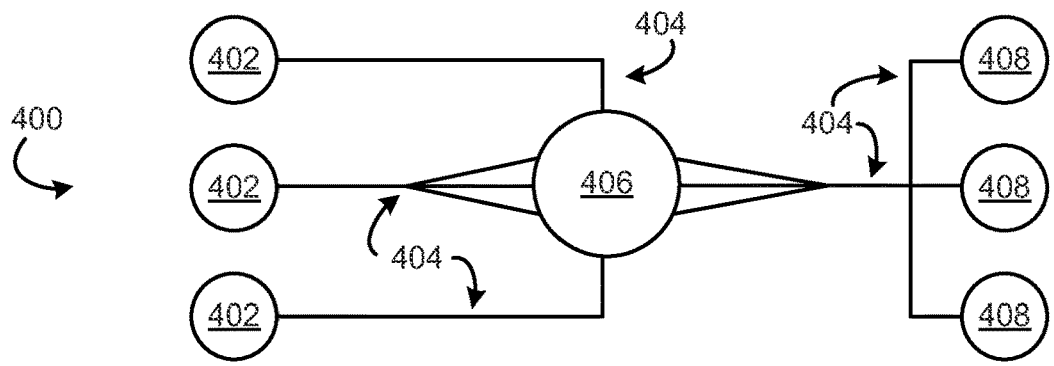
FIG. 4A is a simplified schematic of a fluidic channel arrangement suitable for use in a bioreactor, according to one embodiment.

Referring now to FIG. 4A, one exemplary embodiment of a bioreactor fluidic system 400 is shown, according to a top-down view. The exemplary fluidic system 400 is configured to introduce and/or evacuate one or more fluids to and/or from a bioreactor reservoir 108 using a plurality of inlet ports 402, channels 404, a reservoir port 406 and a plurality of outlet ports 408, in one approach. In preferred arrangements, one or more of the channels 404 may further comprise a plurality of subchannels, depicted in FIG. 4A as a trifurcating branch/convergence immediately adjacent the left and right sides of the reservoir port 406, according to one embodiment. Even more preferably, branching subchannels may facilitate mixing and/or separation of one or more fluids in the channels 404, the reservoir port 406, and/or the reservoir 108, in various embodiments.

In operation, one or more fluids may be introduced to a bioreactor reservoir 108 (e.g. from an external pump, fluidic system, reservoir, etc. as would be understood by one having ordinary skill in the art) via one or more of the inlet ports 402 and channels 404. Each inlet port 402 may be specifically designated and/or utilized to individually introduce one or more unique fluids (e.g. cell growth media, target chemicals, cell suspensions, biomarkers, water, salt solution, etc. as described herein further as would be understood by one having ordinary skill in the art upon reading the present descriptions) to the reservoir 108 via reservoir port 406. Additionally and/or alternatively, one or more inlet ports 402 may be utilized to introduce the same or similar fluids to the reservoir 108 via the reservoir port 406.

Similarly, one or more fluids may be evacuated from a bioreactor reservoir 108 (e.g. using an external pump, fluidic system, reservoir, etc. as would be understood by one having ordinary skill in the art) via one or more of the outlet ports 408 and channels 404. Each outlet port 408 may be specifically designated and/or utilized to individually evacuate one or more unique fluids (e.g. cell growth media, target chemicals, cell suspensions, biomarkers, water, salt solution, cell waste, etc. as described herein further as would be understood by one having ordinary skill in the art upon reading the present descriptions) from the reservoir 108 via reservoir port 406 and channels 404. Additionally and/or alternatively, one or outlet ports 408 may be utilized to evacuate the same or similar fluids from the reservoir 108 via the reservoir port 406.

Figure 4B:
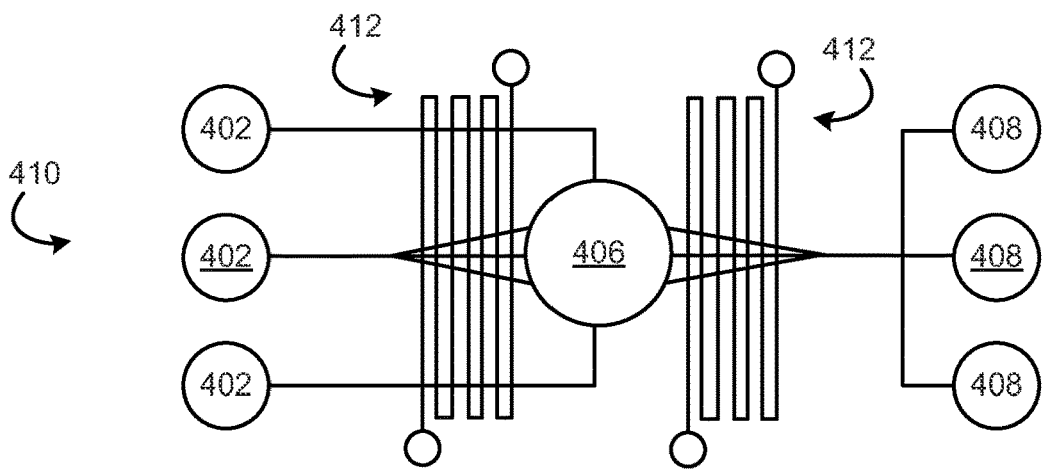
FIG. 4B is a simplified schematic of a fluidic channel and gas-exchange channel arrangement suitable for use in a bioreactor, according to one embodiment.
Figure 4C:
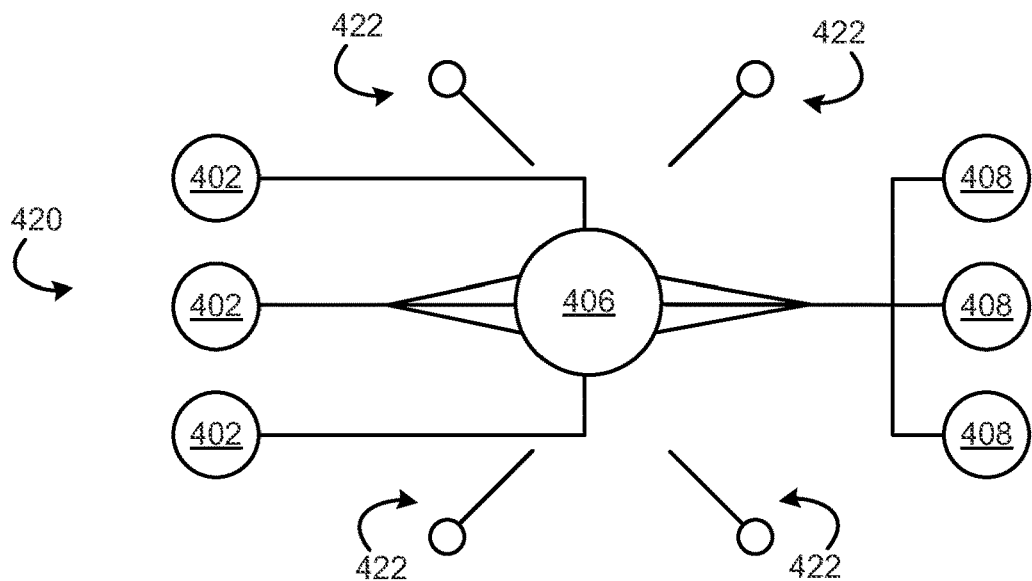
FIG. 4C is a simplified schematic of a fluidic channel and gas-exchange channel arrangement suitable for use in a bioreactor, according to one embodiment.

Referring now to FIGS. 4B and 4C, several illustrative embodiments of a fluidic system 410, 420 including gas exchange channels 412, 422, respectively, are shown from a top-down view. In each embodiment, as well as variations thereof within the scope of the present disclosures, gas exchange channels 412, 422 may be partially or completely disposed in one or more walls 106 of the bioreactor assembly discussed herein. Moreover, the gas exchange channels may be disposed in a same and/or different plane of depth with respect to the fluidic channels 404, inlet ports 402 and/or outlet ports 408 according to the top-down perspective shown in FIGS. 4A-4D.

Preferably, each gas exchange channel 412, 422 includes at least one inlet/outlet port (indicated by the circular termini of the channels 412 and terminus of channels 422, respectively) configured to facilitate exchange of one or more gases between an internal environment of the bioreactor (e.g. the reservoir 108) and the ambient environment, one or more gas sources (such as a $CO_2$ supply, in one approach), and/or other components of the bioreactor (e.g. between the internal environment of the reservoir 108 and a bioreactor enclosure internal environment, in one embodiment).

The gas exchange channels 412, 422 may be arranged in any suitable configuration to facilitate gas exchange between various components of the bioreactor assembly disclosed herein and external environments, gas sources, etc. as would be understood by skilled artisans reading the present descriptions. In one preferred embodiment, the gas exchange channels 412 may be arranged as shown in FIG. 4B, i.e. in a serpentine path passing over portions of one or more channels 404 as viewed from the top-down perspective shown therein. Additionally and/or alternatively, gas exchange channels 422 may be arranged in a linear path extending generally in a direction extending from an interior region of the reservoir (e.g. near the reservoir port 406).

In other embodiments, bioreactors 102 may include one or more heating element(s) 432, alternatively and/or in addition to the fluidic channel(s) 404 and/or gas-exchange channels 412, 422 described above. One such configuration 430 is shown from top-down view in FIG. 4D, according to one embodiment. Any suitable heating mechanism element may be used, including a resistive heater, in some approaches.

Figure 4D:
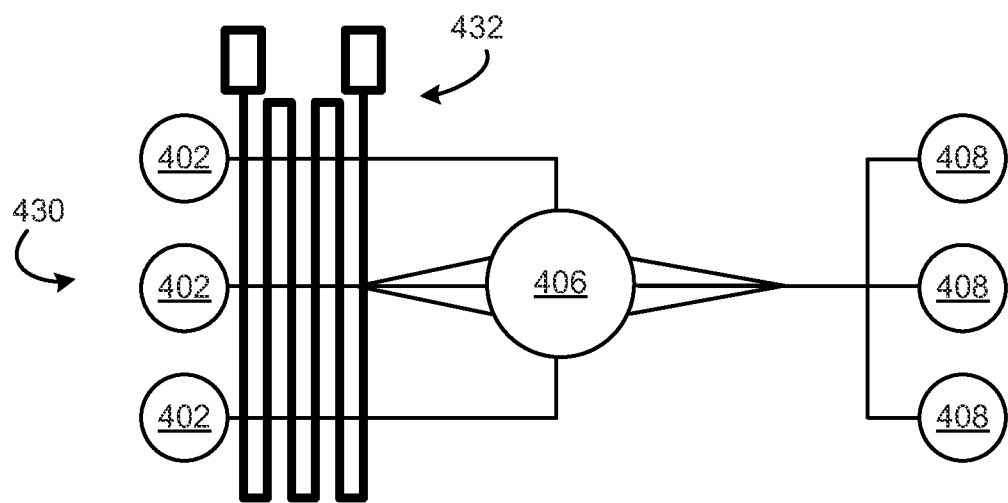
FIG. 4D is a simplified schematic of a fluidic channel and resistive-heater arrangement suitable for use in a bioreactor, according to one embodiment.

While the perspective shown in FIG. 4D depicts apparent overlap between the resistive heater 432 and the fluidic channels 404, in various embodiments the heater 432 and fluidic channels 404 are not positioned in the same plane of depth, as apparent from viewing FIG. 4D. For example, in one approach the fluidic channels 404 may be disposed in one or more of the walls of the bioreactor (e.g. walls 106 as shown in FIGS. 1-2E), while the resistive heater 432 may be disposed in and/or on a surface of an enclosure (e.g. enclosure 124 as shown in FIG. 1) distinct from the walls of the bioreactor. Of course, the heating element 134 may be positioned in any suitable location and/or configuration to effectively influence the temperature of the bioreactor, in various approaches.

Base Assembly

Figure 5:
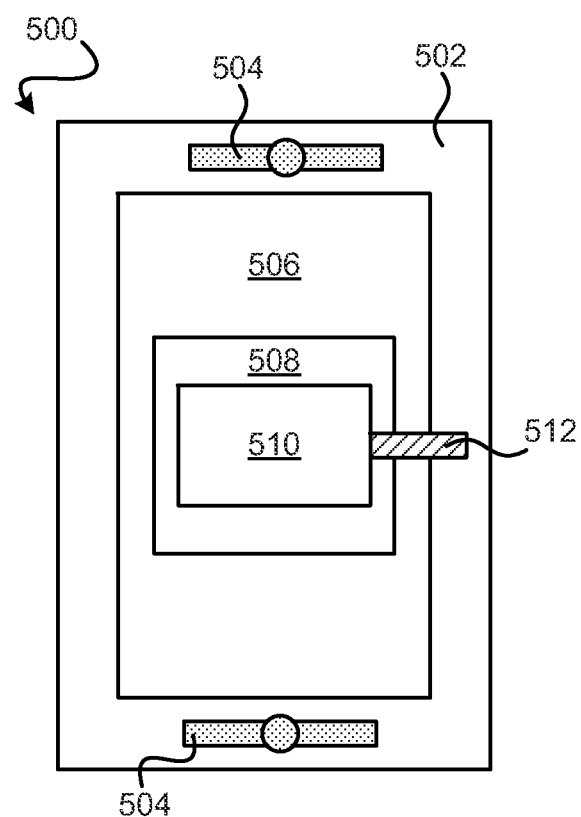
FIG. 5 is a simplified schematic of a bioreactor base plate, substrate and control board assembly, according to one embodiment.

Turning now to FIG. 5, a base assembly 500 is shown, according to one embodiment. As depicted in FIG. 5, base assembly 500 includes a base plate 502 having two locking mechanisms 504, one each located on opposite sides of an upper surface of base plate 502 and configured to engage and reversibly secure in position a bioreactor assembly (not shown) on the base plate 502. The base plate 502 preferably includes a plurality of depressions 506, 508, 510 and a groove 512 extending between at least a part of each of the depressions 506, 508, 510. Preferably, the groove 512 extends along a single line segment from an innermost depression 510 through a middle depression 508 and out to outermost depression 506. The groove 512, regardless of spatial configuration, is configured to facilitate placing and/or removing one or more bioreactor components into the base assembly 500, e.g. using a stylus, spatula, forceps, or other suitable tool as would be understood by one having ordinary skill in the art upon reading the present descriptions.

While the depressions 506, 508, 510 may be any suitable shape (e.g. triangular, square, circular, ovular, hemispherical, ovoid, pentagonal, hexagonal, etc.) to engage a corresponding bioreactor component (as discussed in further detail below), in preferred approaches each of the depressions is substantially rectangular in shape. In even more preferred approaches, the depressions 506, 508, 510 are concentric, regardless of shape. The depressions 506, 508, 510 may have the same shape, similar shapes, or different shapes, in various embodiments, and may or may not be concentric whether or not each depression is similar in shape. The innermost depression 510 may comprise a hole or window in the base plate 502, in one embodiment. The hole or window is preferably configured to facilitate optical observation of a bioreactor 102 coupled to the base assembly 500 (e.g. via, a viewing port of the reservoir 108 as described above). If innermost depression 510 is a window, then it may comprise a material identical or similar to those suitable for use in bioreactor walls 106 and/or the reservoir viewing port as discussed herein (particularly with reference to FIG. 1, above).

Similarly, the middle depression 508 may have an upper face slightly raised from a bottom surface of the base plate 502, as measured with respect to an upper face of the innermost depression 510 (which may be in a same plane as the bottom surface of the base plate, e.g. in embodiments where the innermost depression is a hole in the base plate 502), and is preferably configured to engage a bioreactor substrate, such as substrate 104 described above and depicted in FIGS. 1-2E, in various embodiments.

Outermost depression 506 may have an upper face slightly raised from the bottom surface of the base plate 502, as measured with respect to the upper face of the middle depression 508, and is preferably configured to engage a bioreactor control board, such as control board 600 described below and depicted in FIG. 6, according to one embodiment.

In one particularly preferred embodiment, the innermost depression 510 comprises a rectangular hole in base plate 502 and is located approximately at the center of the base plate 502. Middle depression 508 comprises a rectangular shape and has an upper face that is slightly elevated from the bottom surface of the base plate 502 with respect to the upper face of the innermost depression 510. Outermost depression 506 comprises a rectangular shape and has an upper face slightly elevated from the bottom surface of the base plate 502 with respect to the upper face of the middle depression 508. The perimeter of the base plate 502 and each of the depressions 506, 508 510 forms a series of concentric rectangles. The base plate 502 further comprises an outermost region having an upper face slightly raised from the bottom surface of the base plate with respect to the upper face of the outermost depression 506. The outermost region features two locking mechanisms 504, which are rotatably-mounted on the base plate 502 to engage a bioreactor assembly and secure said assembly in position on the base assembly 500. The groove 512 is rectangular, and extends at a gradual, constant vertical slope from the bottom surface of the base plate 502 to the upper surface of the outermost region of the base plate 502, effectively providing access to each of the depressions 506, 508, 510 and/or any component of the base assembly 500 and/or bioreactor assembly situated therein, respectively.

Control Board

Figure 6:
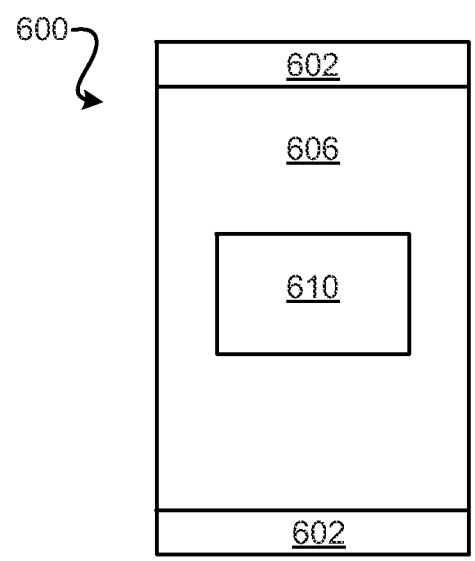
FIG. 6 depicts a simplified schematic of the substrate and control board assembly shown in FIG. 5, according to one embodiment.

Though not shown in FIG. 1, the bioreactor 102 system may also include a control board (e.g. as shown in FIGS. 6 and 7, and described in further detail below) configured to facilitate communication between the bioreactor 102 and a processor via a plurality of electrical interconnect pads 122 in the control board; and to facilitate communication between one or more of the sensors 116 and the control board.

Turning now to FIG. 6, a control board assembly 600 is shown, according to one embodiment. As depicted in FIG. 6, the control board assembly 600 includes a central depression 610, which is preferably configured to at least partially overlap innermost depression 510 of the base assembly 500 and facilitate optical observation and/or visual inspection of a bioreactor 102 positioned near the central depression 610 (e.g. to observe cells 120 in a bioreactor reservoir 108 via the optical viewing port thereof, as described herein).

The control board assembly 600 also includes a base 606 in which the central depression 610 is formed. Control board base 606 may be configured in any suitable shape, and is preferably configured to engage and fit snugly (but removably) in the middle depression 508 of base assembly 500. The control board base 606 may comprise any suitable material that would be recognized by a skilled artisan reading the present descriptions, and in one particularly preferred approach comprises a polymer typically considered suitable for use in forming a base of a printed circuit board (PCB). Coupled to the control board base 606, and preferably extending vertically therefrom along a same plane as an upper face of the control board base 606, are two wings 602. The wings 602 are each configured to engage one of the locking mechanisms 504 of the base assembly 500, in a preferred embodiment.

With continuing reference to the control board 600, any suitable component for providing individual and/or group control of various sensors 116, sensors, gas-exchange and fluidic components described herein may be utilized, in various approaches. In a preferred embodiment, however, the control board includes a printed circuit board (PCB) with circuitry/hardware configured to provide individual control of the aforementioned components.

In one embodiment, the PCB may preferably have dimensions of approximately 76.2 mm by 60 mm. The PCB includes a plurality of omnetics connectors arranged on the control board to facilitate coupling the control board to an external device for communicating operational instructions and/or experimental data between the bioreactor 102 and an external device. Exemplary external devices include laboratory equipment and computer workstations, for example the AlphaLab SnR Multi-Channel 110 workstation, available from Alpha Omega Co. USA, Inc., 5755 North Point Pkwy, Unit 229, Alpharetta Ga. 30022, USA; and various neurophysiology instrumentation platforms offered by Tucker David Technologies (TDT Systems), 11930 Research Circle, Alachua, Fla. 32615 (USA), including the RZ2 Multi-Channel Neurophysiology Workstation.

The PCB also includes a plurality of circuit paths between the omnetics connector and a plurality of electrical interconnect pads 122 arranged on the PCB to facilitate communicating operational instructions and/or experimental data between a plurality of sensors in one or more reservoirs 108 of a bioreactor 102 and the external device. For example, the connector may be configured to accommodate eight individual reservoirs 108 on a single bioreactor platform, and simultaneously control the sensors of each reservoir 108 independently from the others.

The control board, in some embodiments, is generally configured to interface with and/or couple to the bioreactor 102 assembly discussed herein. For example, in one approach the control board 600 may additionally include one or more pins (not shown in FIG. 6, but see pin 702 as depicted in FIG. 7) configured to facilitate electrical communication between interconnect pads 122 coupled to the sensors 116 and an external control device, e.g. via a communication interface (not shown in FIG. 6 but see communication interface 704 as described below and depicted in FIG. 7).

In some embodiments, the control board may be configured to interface with and/or couple to a bioreactor 102 having a single reservoir 108 fluidics system, as shown in the figure below. Configurations of this type may also include up to 128 sensors 116 for simultaneously stimulating cells 120 and/or obtaining experimental data. Moreover, the reservoir 108 and/or sensor array components can be separated from the control board, and autoclaved independently, without causing any damage to the electronic components (e.g. PCB(s) and/or communications ports such as omnetics connectors, discussed above). This enables use of conventional sterilization techniques without reducing the utility of the device or requiring costly replacement of damaged devices.

Bioreactor Assembly

Several illustrative embodiments of a bioreactor assembly, including some or all of the foregoing components will now be described with particular reference to FIG. 7. The exemplary embodiments described below are provided for illustrative purposes and should not be construed as limiting on the scope of the presently disclosed inventive concepts.

The bioreactor components discussed above may be substantially similar as those described herein with reference to FIGS. 1-6 in various approaches, including sensors 116 (or arrays thereof), interconnect pads 122, fluidic channels 110, gas-exchange channels (not shown), inlet(s) 112, outlet(s) 114, heaters (not shown), a control board 706, support structures 128, a substrate 104, walls 106, communication interface(s) 704, etc. as would be understood by one having ordinary skill in the art upon reading the present descriptions.

A side view of a completely assembled in-vitro tissue bioreactor platform 700 is shown in FIG. 7, according to one embodiment. The completed assembly includes a support structure or structures 128 (which may be part of a baseplate 500 described above with reference to FIG. 5), into which a glass substrate 104 such as a slide or coverslip may be removably mounted. The glass substrate may additionally and/or alternatively serve as a substrate onto which sensor(s) 116, interconnect pads 122, and/or conductive pathways therebetween are formed. A control board 706, such as (e.g. control board 600 described above with reference to FIG. 6).

The assembled platform 700 also includes a pin 702 (such as a Pogo-pin) configured to facilitate communication between electrical interconnect pads 122 and the communication interface 704. The communication interface 704, in turn, is positioned and configured to facilitate communicating operational instructions and/or experimental data between an external device to which the reactor is coupled and the various components of the reactor itself (such as the sensors 116, fluidic systems, etc). The pin(s) 702 and communication interfaces 704 thus represent an interface between the platform 700 and the controlling external device.

Of course, the communication interface 704 is merely one example of an electrical connection that can be used on various embodiments of an assembled bioreactor platform 700. Any form of electrical connection can be soldered to the control board 706 to create a connect on between the bioreactor 102 and the external device may be utilized, as will be appreciated by one having ordinary skill in the art upon reading the present descriptions.

The assembly 700, in preferred embodiments also includes a reservoir 108 positioned such that a cell-adhesion surface of the reservoir 108 (which is the surface having the sensor(s) 116 formed thereon) is characterized by an optical viewing window (depicted by the gap between support structures 128 in FIG. 7) configured to facilitate observing and/or gathering optical data from the reservoir 108.

Operational Methodologies

Having described various embodiments of the inventive systems disclosed herein, we now turn to describing exemplary embodiments of methods for using the in-vitro tissue bioreactor 102.

Figure 10:
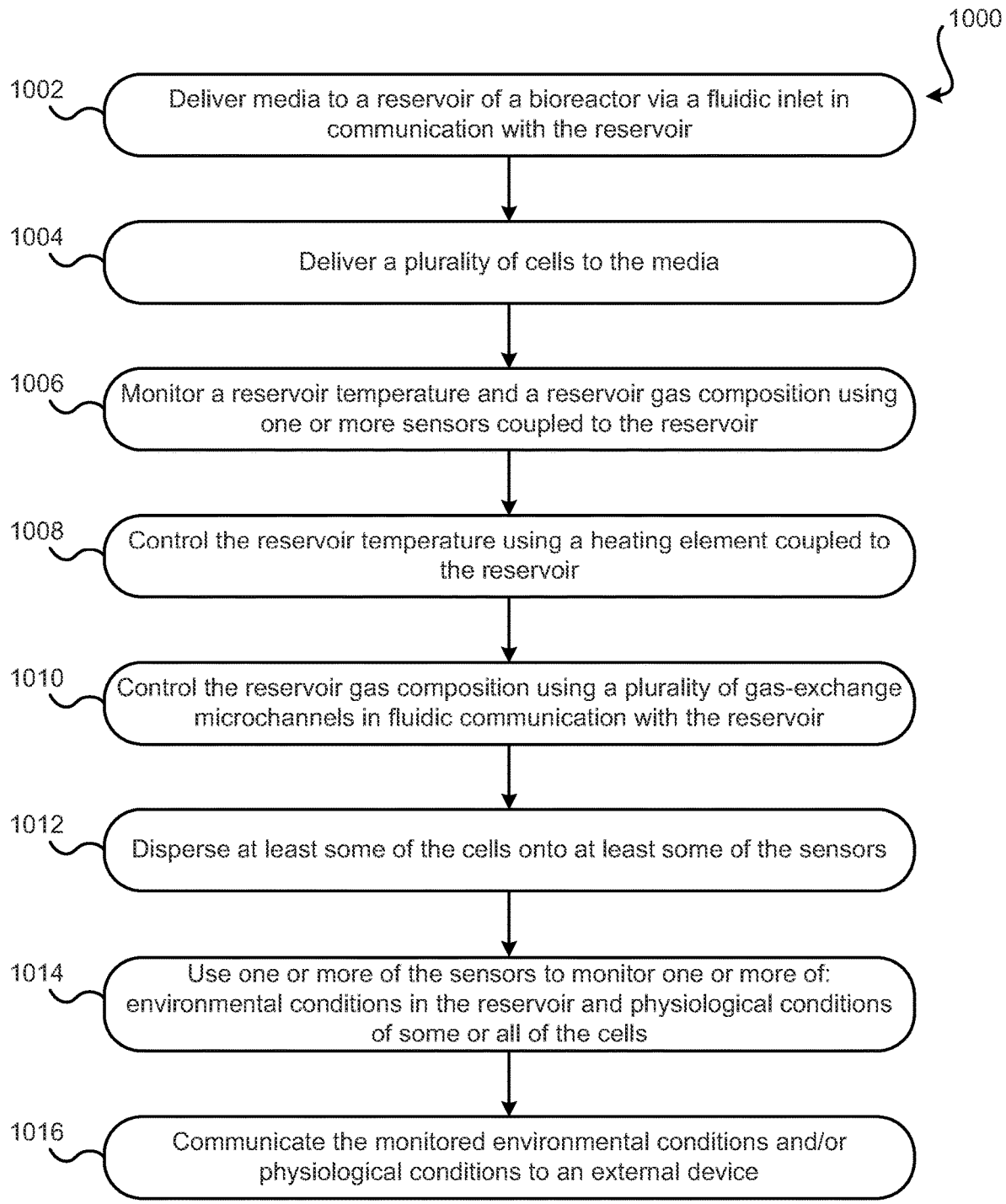
FIG. 10 is a flowchart of a method, according to one embodiment.

In one embodiment, and as shown according to the flowchart depicted in FIG. 10, a method 1000 may include one or more of the following exemplary operations, in any suitable order and/or combination, as would be understood by one having ordinary skill in the art upon reading the present descriptions. Moreover, the method 1000 may be performed in any suitable environment, including those depicted in FIGS. 1-9D, in various approaches.

In one embodiment, method 1000 includes operation 1002, where media is delivered to a reservoir 108 of a bioreactor 102, e.g. via a fluidic inlet 112 in fluidic communication with the reservoir 108. Media may be delivered according to any suitable mechanism or technique known in the art, and preferably in a manner and/or using mechanisms compatible with an automated fluidic system such as described herein.

In another embodiment, method 1000 additionally and/or alternatively includes operation 1004, where a plurality of cells 120 are delivered to the media. Cells 120 may be delivered to the media via any suitable mechanism or technique, such as being delivered through fluidic channels in a cell culture medium, dispensed manually in a cell culture medium (e.g. via serological pipettor, micropipettor, etc.), by directly inoculating the delivered media in the reservoir using known techniques, etc. as would be understood by one having ordinary skill in the art upon reading the present descriptions.

In yet another embodiment, method 1000 additionally and/or alternatively includes operation 1006, where a reservoir 108 temperature and a reservoir 108 gas composition are monitored using one or more sensors 116 coupled to the reservoir 108. For example, the reservoir temperature may be monitored using a thermometer or other thermal sensor to detect deviations in environmental temperature from a desired temperature, such as a physiological temperature (e.g. 37 centigrade, in one embodiment). Similarly, gas composition may be monitored using one or more sensors to detect deviations from a predetermined composition with respect to one or more gases such as molecular oxygen ($O_2$), carbon monoxide (CO), carbon dioxide ($CO_2$), molecular nitrogen ($N_2$), vaporous water (e.g. measuring humidity), etc. as would be understood by one having ordinary skill in the art upon reading the present descriptions.

In still another embodiment, method 1000 additionally and/or alternatively includes operation 1008, where the reservoir 108 temperature is controlled using a heating element coupled to the reservoir 108. For example, in various approaches a reservoir temperature may be adjusted upon detecting a drop in temperature from a predetermined incubation temperature. In response to detecting the temperature drop, a heating element such as a resistive heater 432 may be activated to generate heat and restore the reservoir environmental temperature to the predetermined incubation temperature.

In still yet another embodiment, method 1000 additionally and/or alternatively includes operation 1010, where the reservoir 108 gas composition is controlled using a plurality of gas-exchange channels 130 in fluidic communication with the reservoir 108. For example, one or more gases such as described above with respect to monitoring gas composition may be supplied to the reservoir from one or more gas supply sources in fluidic communication with the reservoir via the gas-exchange channels 130. Similarly, gas maybe evacuated or vented away from the reservoir 108 via the gas-exchange channels 130, in additional and/or alternative arrangements.

In more embodiments, method 1000 additionally and/or alternatively includes operation 1012, where at least some of the cells 120 are dispersed onto at least some of the sensors 116. Cells may be dispersed naturally in the course of delivering the cells to the media as described above with respect to operation 1004, in some approaches.

In other approaches, cell dispersal onto sensors 116 may be facilitated by functionalizing the sensor surface(s), for example with a material designed to facilitate cell surface adhesion to the sensor surface, and/or by customizing the physical configuration of the sensors 116. Customizing the physical configuration may include manipulating sensors with respect to spacing and physical location in an organized array such as shown in FIG. 3. Additionally and/or alternatively, customizing the physical configuration of sensors may include manipulating the shape of the sensor itself, (e.g. where individual sensors have a ring configuration). In still more approaches, cell dispersal onto one or more sensors may be encouraged by applying slight vacuum to the reservoir (e.g. via one or more vacuum channels 134 as shown in FIG. 2E).

In additional and/or alternative embodiments, method 1000 includes operation 1014, where one or more of the sensors 116 are used to monitor one or more of: environmental conditions in the reservoir 108; and physiological conditions of some or all of the cells 120. The sensors may be controlled via an external device in communication with the sensors via, for example, one or more of interconnect pads 122, pins 702, communication interfaces 704, and or any appropriate conductive pathways therebetween, in various embodiments. Monitoring environmental conditions may include monitoring concentration of one or more target chemicals in the cell media, monitoring media pH, monitoring physical properties of the cell media, e.g. viscosity, temperature, etc., monitoring reservoir gas composition, etc. as would be understood by one having ordinary skill in the art upon reading the present descriptions. Monitoring physiological conditions may include monitoring individual cell morphology and/or cell population morphology (e.g. formation of extracellular matrices), monitoring cell osmolarity, monitoring expression of one or more proteins, nucleic acids, etc., as would be understood by one having ordinary skill in the art upon reading the present descriptions.

In various approaches, method 1000 additionally and/or alternatively includes communicating the monitored environmental conditions and/or physiological conditions to an external device in operation 1016. The conditions may be communicated using any suitable technique and/or mechanism described herein and/or any communication technique/mechanism that a person having ordinary skill in the art would appreciate to be suitable for communicating monitored environmental and/or physiological conditions between an external device and the bioreactor, upon reading the present descriptions.

In particularly preferred embodiments of method 1000, the bioreactor 102 is integrated into a platform having a width in a range from approximately 50 mm to approximately 150 mm and a depth in a range from approximately 60 mm to approximately 100 mm.

In more embodiments, using the in-vitro tissue bioreactor 102 may additionally and/or alternatively include one or more optional operations, such as evacuating the media from the reservoir 108 via a fluidic outlet 114 in fluidic communication with the reservoir 108 (preferably without evacuating the cells 120 from the reservoir 108); and delivering new media to the reservoir 108.

In still more embodiments, using the in-vitro tissue bioreactor 102 may additionally and/or alternatively include stimulating at least some of the cells 120 using the sensors 116, monitoring the stimulated cells 120 to detect a physiological response to the stimulation; and/or communicating any detected physiological response to the external device. The sensors 116 used to stimulate the cells 120 may be arranged in a configuration selected from a group consisting of: ring-shaped structures and a three-dimensional matrix of nanowires arranged throughout the reservoir 108.

In embodiments where the sensors 116 are arranged in a three-dimensional matrix of nanowires, monitoring one or more of the environmental conditions and the physiological conditions may be performed in three dimensions using the plurality of nanowire sensors.

In preferred embodiments, while using the presently disclosed in-vitro tissue bioreactor 102, each of the following operations are preferably performed under the automated control of an external device: delivering the media; delivering a plurality of cells 120 to the media; monitoring a reservoir 108 temperature and a reservoir 108 gas composition using one or more sensors 116 coupled to the reservoir 108; controlling the reservoir 108 temperature using a heating element coupled to the reservoir 108; controlling the reservoir 108 gas composition using a plurality of gas-exchange channels 110 in fluidic communication with the reservoir 108; using one or more of the sensors 116 to monitor one or more of: environmental conditions in the reservoir 108; and physiological conditions of some or all of the cells 120 dispersed on the sensors 116; and communicating the monitored environmental conditions and/or physiological conditions to the external device.

Practical Applications

The presently disclosed technology has many useful applications, including those discussed above, as well as Drug screening, pharmaceutical testing, in-vitro, human-relevant tissue, tissue surrogates, drug delivery, toxicology, pharmacology, fluidics, environmental control, microreactor studies, electrical stimulation and recording, optical imaging, temperature control, gas control, etc.

In preferred approaches, the presently disclosed in-vitro tissue bioreactor 102 platform is capable of maintaining a physiologically relevant cell population for 21 days or more. A cell population is "physiologically relevant" so long as cells 120 remain a suitable approximation of actual human cells 120 as they exist in vivo to conduct experiments and generate data representative of what would be similarly observed from tissues and/or organ systems in the human body.

While various embodiments have been described above, it should be understood that they have been presented by way of example only, and not limitation. Thus, the breadth and scope of an embodiment of the present invention should not be limited by any of the above-described exemplary embodiments, but should be defined only in accordance with the following claims and their equivalents.

What is claimed is:

1. A system, comprising:
   a bioreactor coupled to a substrate, the bioreactor comprising:
   a plurality of walls defining a reservoir;
   a plurality of fluidic channels in at least some of the walls;
   a fluidic inlet in fluidic communication with the reservoir via the fluidic channels;
   a fluidic outlet in fluidic communication with the reservoir via the fluidic channels; and
   a plurality of sensors coupled to the reservoir, at least some of the sensors each independently comprising a ring characterized by a diameter in a range from about 30 μm to about 90 μm, and each of the sensors being independently configured to monitor either or both of:
   environmental conditions in the reservoir; and
   physiological conditions of one or more cells when the one or more cells are present in the reservoir, wherein monitoring the physiological conditions of the one or more cells comprises: monitoring an individual morphology of some or all of the one or more cells, monitoring a population morphology of the one or more cells, monitoring an osmolarity of some or all of the one or more cells, monitoring an expression of one or more proteins by the one or more cells, and/or monitoring an expression of one or more nucleic acids by the one or more cells; and a base plate coupled to the substrate, the base plate comprising:
  a plurality of concentric depressions, at least one of the depressions being configured to engage the substrate, an outermost of the depressions being configured to engage a control board of the bioreactor, and an innermost of the depressions comprising a hole in the base plate;
  a groove extending from the innermost of the depressions to the outermost of the depressions, the groove being configured to facilitate placing and/or removing components of the bioreactor into the base plate; and
  a plurality of locking mechanisms configured to secure the bioreactor to the base plate; and
wherein the reservoir is arranged to receive at least media and the one or more cells directly from the fluidic channels.

2. The system as recited in claim 1, wherein the sensors comprise:
  optical sensors configured to detect one or more optical conditions within the reservoir;
  mechanical sensors configured to detect one or more mechanical forces acting on contents of the reservoir;
  electrical sensors configured to detect one or more electrical forces acting on contents of the reservoir; and
  sensors comprising a material selected from the group consisting of: indium oxide, and activated iridium oxide.

3. The system as recited in claim 2, wherein the mechanical forces are selected from the group consisting of: shear stress, surface tension, and
  physical strain on the one or more cells; and
  wherein the optical conditions comprise detecting an amount of light emitted by the one or more cells, wherein the light is characterized by a predetermined wavelength.

4. The system as recited in claim 1, comprising a plurality of the bioreactors, wherein the bioreactors are coupled to the substrate; and
  a control board configured to:
    facilitate communication between the system and a processor; and
    independently control the bioreactors, wherein controlling the bioreactors comprises: controlling delivery of media to the reservoirs of the bioreactors, controlling delivery of cells to the reservoirs of the bioreactors, controlling a temperature of the reservoirs of the bioreactors, and controlling a gas composition of the reservoirs of the bioreactors.

5. The system as recited in claim 1, further comprising:
  a plurality of openings in one of the walls, the openings configured to facilitate: adding one or more of cells and reagents directly to the reservoir via the fluidic channels, removing one or more of cells and reagents directly from the reservoir via the fluidic channels, and transferring fluid directly between the reservoir and another reservoir via the fluidic channels; and
  a plurality of plugs, each plug being adapted to engage one of the openings and selectively control gas exchange and material exchange between the reservoir and an environment external to the reservoir.

6. The system as recited in claim 1, wherein the fluidic inlet, the fluidic outlet, and the reservoir are configured to mix one or more fluids in the reservoir.

7. The system as recited in claim 1, wherein the substrate comprises an optically transparent viewing window configured to transmit optical information from the reservoir.

8. The system as recited in claim 1, further comprising: a gas-source in communication with the reservoir via a plurality of gas exchange channels formed in at least one of the walls.

9. The system as recited in claim 1, wherein the walls comprise either or both of: dielectrics, and spin-on-glass.

10. The system as recited in claim 1, further comprising a heat source in thermal communication with the reservoir, the heat source comprising:
  a heating chamber comprising temperature control, the heating chamber surrounding the bioreactor.

11. The system as recited in claim 1, further comprising integrated electronics configured to perform environmental control, fluidic processing and control, sensing and stimulating cells functionalities.

12. The system as recited in claim 1, wherein the sensors further comprise a planar array of the sensors characterized by an inter-sensor spacing in a range from 100 μm to 500 μm.

13. A method, comprising:
  delivering media to the reservoir of the bioreactor of the system as recited in claim 1;
  delivering a plurality of cells to the reservoir, wherein at least some of the cells are disposed onto one or more of the plurality of sensors coupled to the bioreactor;
  controlling a temperature and a gas composition within the reservoir;
  using one or more of the plurality of sensors to monitor either or both of:
    the environmental conditions in the reservoir; and
    the physiological conditions of at least some of the cells when the one or more cells are present in the reservoir; and
  communicating the monitored environmental conditions and/or the monitored physiological conditions to an external device.

14. The system as recited in claim 1, wherein at least some of the sensors are present in the form of one or more nanowires arranged in a three-dimensional matrix throughout the reservoir.

15. The system as recited in claim 1, wherein the ring is configured to facilitate at least some of the one or more cells nestling in an interior region of each respective ring structure.

16. The system as recited in claim 1, wherein the sensors are configured to electrically stimulate the one or more cells when the one or more cells are present in the reservoir.

17. The system as recited in claim 1, wherein the fluidic inlet and the fluidic outlet are offset from one another in three spatial dimensions to facilitate forming a vortex effect in the reservoir.

18. The system as recited in claim 1, further comprising:
  a gas-source in communication with the reservoir via a plurality of channels in at least one of the walls; and
  a heat source in thermal communication with the reservoir, the heat source comprising either or both of:
    a resistive heater embedded in the substrate; and
    a heating chamber comprising temperature control, the heating chamber surrounding the bioreactor; and
  wherein the sensors are arranged in a three-dimensional pattern.

19. The system as recited in claim 4, wherein the control board comprises:
- a printed circuit board having a central region configured to facilitate optical observation of the one or more cells when the one or more cells are present in the reservoir;
- a plurality of omnetics connectors configured to couple the control board to an external device and communicate operational instructions between the bioreactor and the external device; and
- a plurality of electrical interconnect pads configured to facilitate communicating operational instructions between the sensors coupled to the reservoir and the external device.

20. The system as recited in claim 1, wherein the sensors comprise a material selected from the group consisting of: indium oxide and activated iridium oxide.

21. The system as recited in claim 1, wherein at least some of the sensors further comprise a functionalized self-assembled monolayer selectively patterned onto a surface of the sensors.

22. The system as recited in claim 1, wherein at least some of the sensors are functionalized to detect one or more chemicals of interest; and wherein the functionalization comprises inclusion of dopamine sensors.

* * * * *